(12) United States Patent
de Keczer et al.

(10) Patent No.: US 6,783,947 B1
(45) Date of Patent: Aug. 31, 2004

(54) PROTECTING GROUPS FOR BIOLOGICAL LABELING

(75) Inventors: Steve de Keczer, Saratoga, CA (US); Yen Ping Liu, Cupertino, CA (US); Dariush Davalian, San Jose, CA (US); Nurith Kurn, Palo Alto, CA (US); Edwin F. Ullman, Atherton, CA (US)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 09/393,579

(22) Filed: Sep. 9, 1999

(51) Int. Cl.$^7$ ............... G01N 33/546; G01N 33/577
(52) U.S. Cl. ............ 435/7.93; 435/7.5; 435/975; 436/531; 436/815; 436/825
(58) Field of Search .................. 435/7.5, 7.93, 435/975; 436/531, 815, 825; 562/587

(56) References Cited

U.S. PATENT DOCUMENTS

| | | | |
|---|---|---|---|
| 3,679,655 A | 7/1972 | Jager et al. | 260/112.5 |
| 3,794,633 A | 2/1974 | Kamber et al. | 260/112.5 |
| 3,932,489 A | 1/1976 | Smithwick, Jr. | 260/482 |
| 4,038,306 A | 7/1977 | Milkowski et al. | 260/47.9 |
| 4,271,068 A | 6/1981 | Kamber et al. | 260/112.5 |
| 4,337,194 A | 6/1982 | Diaz et al. | 260/112.5 |
| 4,507,251 A | 3/1985 | Soriano et al. | 260/94.4 |
| 4,599,407 A | 7/1986 | Wunsch | 544/85 |
| 4,786,684 A | 11/1988 | Glass | 525/54.1 |
| 4,803,156 A | 2/1989 | Neurath et al. | 435/7 |
| 4,965,343 A | 10/1990 | Felix et al. | 530/334 |
| 5,066,716 A | 11/1991 | Robey et al. | 525/54.1 |
| 5,120,898 A | 6/1992 | Baba et al. | 515/750 |
| 5,212,157 A | 5/1993 | Anderson et al. | 514/17 |
| 5,292,669 A | 3/1994 | Guder et al. | 435/48 |
| 5,439,792 A | 8/1995 | Blake et al. | 435/5 |
| 5,478,729 A | * 12/1995 | Van Atta et al. | 435/7.93 |
| 5,536,815 A | 7/1996 | Carpino et al. | 530/535 |
| 5,543,507 A | 8/1996 | Cook et al. | 536/23.1 |
| 5,700,910 A | * 12/1997 | Metzger et al. | 530/338 |
| 5,714,361 A | 2/1998 | Widlanski | 435/184 |
| 5,759,993 A | 6/1998 | Venot et al. | 514/8 |

FOREIGN PATENT DOCUMENTS

WO   WO 97/36616   10/1997

OTHER PUBLICATIONS

CA No. 57:7553i (1957).*
Morrison & Boyd, "Organic Chemistry" 3rd Ed. (Allyn & Bacon 1973) pp. 562–563.*
CAPLUS AN 1947:25587 to Bergkvist Svensk Kem. Tid. (1947) vol. 59 pp. 24–27.*
CAPLUS AN 1991:631804 and accompany RN's 136454–49–4 and 136454–32–5.*
David, et al.; *J. Chem Soc., Perkins Transactions 1*; Stereoselective Dienyl Ether Synthesis from Melonaldehyde *trans*–Enol Ehters:(*E*)–Buta–1,3–dienyl, and(*E,Z*)– and (*E,E*)–4–Chlorobuta–1,3–dienyl Ethers of a Protected Sugar; Conversion of the Latter into Functionalized Chiral Disaccharide Precursors; pp. 2521–2525, XP002155921 abstract; 1979.
Soullez, et al.; *J. Chem Soc., Perkin Transactions 1*; ω–Halogeno polyenals: preparation and application to a one–pot syntheses of polyenals from corbonyl compounds; pp. 1639–1645; XP002155921; 1997.
Springer, et al.; *European J. Cancer*; GB Pergamon Press, Oxford; Ablation of Human Choriocarcinoma Xenografts in Nude Mice by Antibody–directed Enzyme Prodrug Therapy (ADEPT) with Three Novel Compounds; pp. 1361–1366; XP000645520; Nov. 1, 1991.

* cited by examiner

Primary Examiner—Bennett Celsa
(74) Attorney, Agent, or Firm—Louis C. Cullman; Cynthia G. Tymeson

(57) ABSTRACT

Alpha-haloketones are useful alkylating agents for coupling to sulfhydryl-containing biomolecules. However, they react spontaneously with water, alkali and organic bases and therefore cannot be stored for extended periods of time in aqueous solutions, particularly in the presence of proteins at physiological pH. The present invention provides novel solutions to these problems, however, as novel compounds and compositions comprising protected haloketones are disclosed herein. Methods of preparing and using protected haloketones which are useful in a variety of applications—e.g., in assays and conjugation reactions—are also disclosed herein.

20 Claims, No Drawings

PROTECTING GROUPS FOR BIOLOGICAL LABELING

INTRODUCTION AND BACKGROUND

Alpha-haloketones are alkylating agents that are useful in a variety of contexts, including the coupling of various molecules to other, sulfhydryl-containing molecules. However, the α-haloketones possess characteristics that make them problematical and impractical for use in assays and reactions in which the components of a kit for use in such methods need to be stored together and/or for a period of time. For example, the α-haloketones react spontaneously with water, alkali and organic bases and therefore cannot be stored for extended periods of time in aqueous solutions, particularly in the presence of proteins at physiological pH.

α-Haloketones are often not used because they are generally too reactive, cause cross-linking of the protein, and are otherwise hydrolytically unstable. Were it not for these problems, their higher reactivity would permit the use of lower concentrations of the drug derivative. Some of the α-haloketones are also insufficiently soluble for use in such contexts. Thus, despite their potential usefulness in a number of diagnostic and synthetic applications, the α-haloketones are often considered too unstable to be used in such applications.

Similarly, proteins are often coupled to other proteins by attaching an alkylating group to one protein and a sulfhydryl group to the other. However, it is often difficult to obtain quantitative coupling in this matter without using high concentrations of one or both protein members and/or attaching multiple or single alkylating agents to one of the proteins. Additionally, the protein having alkylating agents attached must either have no sulfhydryl group or its sulfhydryl groups must be protected to avoid polymerization. The problem again could be overcome by using a more reactive α-haloketone if it were not for the difficulty of preparing and storing a protein containing a highly-reactive alkylating agent.

The present invention provides novel solutions to the foregoing problems, however, thereby rendering this class of alkylating agents practical for various diagnostic and synthetic utilities, among others. In conjunction with the disclosure of novel compounds and compositions comprising protected haloketones, the present invention also discloses methods of preparing and using protected haloketones which are useful in a variety of applications—e.g., in assays and conjugation reactions.

As an example of the latter, certain G6PDH drug conjugates are prepared by first coupling the enzyme with an α-haloacid to form an α-haloamide and then coupling this conjugate with a sulfhydryl-labeled drug. The method is particularly useful when the drug has a free amino group that would interfere with coupling by means of an active ester of the drug.

SUMMARY OF THE INVENTION

Therefore, in one embodiment of the invention, protecting groups that permit long-term storage of protected α-haloketones, provide additional water solubility where needed, and offer a simple biocompatible method for removal are disclosed.

Therefore, in one embodiment, the invention discloses a composition comprising a protected alkylating reagent wherein deprotection of the reagent is catalyzed by an enzyme. In various preferred embodiments, the reagent includes a protecting group selected from the group consisting of a phosphate, an ester, a carbohydrate, a nucleic acid, and a lipid. Various preferred embodiments also disclose that the enzyme is selected from the group consisting of glycosidases, nucleases, lipases, esterases, hydroxylases and phosphatases.

In alternative embodiments of the invention, the reagent is a 2-halovinyl ether, a 2-halovinyl ester, a 4-halobutadienyl ether, or a 4-halobutadienyl ester. In various embodiments, the 2-halovinyl ether or ester is a 2-halovinyl monophosphate. In other embodiments, the vinyl group is substituted with one or two alkyl or aryl groups; the alkyl or aryl groups may be substituted or unsubstituted.

In various preferred embodiments of the invention, the haloketone is an α-haloketone. Preferred α-haloketones include α-bromoacetylbenzoic acid (BABA) and α-chloroacetylbenzoic acid (CABA). The compositions of the present invention may further comprise a nucleophilic agent and/or a disulfide reducing agent. Useful disulfide reducing agents include phosphines, such as tris(carboxyethyl)phosphine (TCEP).

The present invention also discloses various kits, such as kits for use in carrying out a coupling reaction. One such kit comprises, in a packaged combination, a first reagent comprising a protected alkylating reagent, in an amount sufficient to conduct at least one reaction.

In one variation, the first reagent includes a protecting group selected from the group consisting of phosphate esters, carboxylate esters, sulfate esters, glycosides and ketals. In another variation, the first reagent includes a protecting group selected from the group consisting of phosphate and carbohydrate. In various embodiments, the first reagent may be a protected haloketone and may comprise a 2-halovinyl ether or ester. An exemplary 2-halovinyl ester is a 2-halovinyl monophosphate.

A protected haloketone of the present invention preferably comprises an α-haloketone, such as BABA or CABA. Alternatively, the first regent may be a 4-halobutadienyl ether or ester. In various embodiments, the vinyl group is substituted with one or two alkyl or aryl groups.

The kit may further comprise a second reagent comprising a catalyst capable of deprotecting the protected alkylating reagent. In various embodiments, the first and second reagents are included in separate containers.

In another variation of the disclosed kits, the catalyst comprises an enzyme. Suitable enzymes for use as disclosed may be selected from the group consisting of glycosidases, nucleases, lipases, esterases, hydroxylases, phosphatases (e.g., alkaline phosphatase) and ribozymes.

The present invention also discloses kits for use in a method for detecting quantitative determination homocysteine in a sample, comprising in a packaged combination: a first reagent comprising a protected alkylating reagent capable of chemically modifying homocysteine to form modified homocysteine when deprotected, a second reagent comprising an activating reagent capable of deprotecting the protected alkylating reagent, and a third reagent capable of specifically binding to the modified homocysteine, each in an amount sufficient to conduct at least one assay.

In various kits of the present invention, the first reagent comprises a protected haloketone having a phosphate protecting group. In various disclosed embodiments, the protected haloketone included in a kit is CABA or BABA. The first reagent may further comprise a homocysteine disulfide reducing agent; it may also further comprise a solid matrix coated with modified homocysteine. The modified homocysteine may be the product formed by deprotecting the protected haloketone and reaction of the deprotected haloketone with homocysteine in the sample. Alternatively, the modified homocysteine may be a 4-carboxyphenacyl thioether of homocysteine (hcy-ABA).

In various alternative embodiments, the solid matrix comprises latex beads, glass beads, a microtiter plate, nitrocellulose, agarose, liposomes, and the like. In embodiments including a homocysteine disulfide reducing agent, that agent may comprise a phosphine. One exemplary phosphine useful in the kits of the present invention is TCEP.

In other embodiments of the kits of the present invention, the second reagent further comprises a phosphatase. In one variation, the phosphatase is alkaline phosphatase. Other variations include kits wherein the second reagent further comprises a solid matrix coated with a receptor capable of specifically binding modified homocysteine. The receptor may comprise an antibody or an immunologically active fragment thereof. When the second reagent further comprises a solid matrix, that matrix may comprise latex beads, glass beads, a microtiter plate, nitrocellulose, agarose, liposomes, and the like.

In the various kits of the present invention, the matrix may further include a signaling agent affixed thereto. Various useful signaling agents include chemiluminescent agents, fluorescent agents, and chromogenic agents, to name a few examples.

In another embodiment, the invention discloses methods of preparing molecular conjugates, comprising the following steps:
(a) labeling a first molecule with a protected alkylating reagent;
(b) admixing the labeled first molecule with a second molecule, wherein the second molecule contains one or more nucleophilic groups attached thereto;
(c) adding an enzyme to the admixture of first and second molecules to initiate a coupling reaction.

In one variation, the first molecule includes an amino or hydroxyl group. The first molecule may be a small molecule or a large molecule (or polymer).

In various embodiments, the second molecule contains a sulfhydryl group. Like the first molecule, the second molecule may be a small molecule (e.g., a lipid or modified lipid) or a large molecule (or polymer). In embodiments in which the second molecule comprises a large molecule or polymer, the large molecule or polymer may be selected from the group consisting of proteins, glycoproteins, lipopolysaccharides, lipoproteins, modified saccharides, and modified nucleic acid molecules.

With respect to the protected alkylating reagent used in the methods of the present invention, that reagent is preferably a haloketone enol phosphate such as CABA (chloro acetyl benzoic acid) enol phosphate or BABA (bromo acetyl benzoic acid) enol phosphate. In another variation of the disclosed methods, the enzyme is a phosphatase, e.g., alkaline phosphatase.

The invention also discloses methods of determining the amount of homocysteine in a sample suspected of containing the homocysteine, comprising the steps of:
(a) bringing together in an aqueous medium:
  (1) the sample,
  (2) a first reagent comprising a protected alkylating reagent capable of being activated to chemically modify the sulfhydryl groups of homocysteine to form modified homocysteine, and
  (3) a second reagent comprising a ligand capable of specifically binding to the modified homocysteine to form an immunocomplex; and
  (4) a third reagent capable of activating the protected alkylating reagent.
(b) measuring the amount of the immunocomplex, the amount thereof being related to the amount of homocysteine in the sample.

In one embodiment, the first reagent further comprises a homocysteine disulfide reducing agent. In another variation, the protected alkylating reagent is a halovinyl ether or ester. One preferred embodiment provides that the halovinyl ether or ester is an α-haloketone enol phosphate. Useful α-haloketone enol phosphates according to the present invention include BABA enol phosphate and CABA enol phosphate.

In other disclosed variations, the third reagent is a phosphatase—e.g., alkaline phosphatase. Moreover, the first reagent may further comprise a solid matrix coated with hcy-ABA and/or a solid matrix coated with a receptor capable of binding modified homocysteine. In embodiments including a solid matrix, the matrix may comprise latex beads, glass beads, a microtiter plate, nitrocellulose, liposomes, agarose, and so forth. Yet another embodiment discloses that the receptor is selected from the group consisting of an antibody or an immunologically active fragment of an antibody.

In another embodiment, the invention discloses methods of determining the amount of homocysteine in a sample, wherein at least a portion of the homocysteine is in the disulfide form, comprising the steps of:
(a) preparing an admixture comprising:
  (1) the sample,
  (2) a releasing agent to release the homocysteine from the disulfide form,
  (3) a protected alkylating reagent capable of being activated to chemically modify the sulfhydryl groups of homocysteine to form modified homocysteine, and
  (4) a receptor capable of specifically binding to the modified homocysteine to form an immune complex; and
  (5) an activating reagent capable of deprotecting the protected alkylating reagent.
(b) examining the medium for the amount of the immunocomplex, the amount thereof being related to the amount of homocysteine in the sample.

According to various disclosed embodiments, the releasing agent may be a phosphine (e.g., TCEP); the protected alkylating reagent may be a halogenated enol phosphate; the receptor may be an antibody or an immunologically active fragment thereof; and the activating reagent may comprise a phosphatase.

Also disclosed herein are methods of preparing a stable, protected haloketone comprising the phosphorylation of the haloketone to form its corresponding enol phosphate. In one embodiment, the protected haloketone is an α-haloketone; BABA and CABA are examples of protected haloketones useful according to the present invention.

The invention further discloses a process for preparing a haloketone enol phosphate, comprising the steps of:
(a) reacting ethyl 4-acetylbenzoate and a halogenating compound to produce a halogenated acetylbenzoate ester;
(b) phosphorylating the ester in THF with phosphoryl chloride in the presence of diisopropylethylamine to produce an enol phosphoryl ester;

(c) treating the enol phosphoryl ester with aqueous sodium hydroxide to produce an enol phosphate ester sodium salt; and (d) treating the enol phosphate ester sodium salt with sodium hydroxide to yield halovinyl enol phosphate benzoic acid sodium salt.

Further disclosed is a method of alkylating a mercaptan in an aqueous solution comprising combining the mercaptan with an enol ester of an α-haloketone or the enol ester of an γ-halo-α,β-unsaturated ketone, and an enzyme capable of hydrolyzing the enol ester.

The invention also discloses a protected haloketone according to the following formulation:

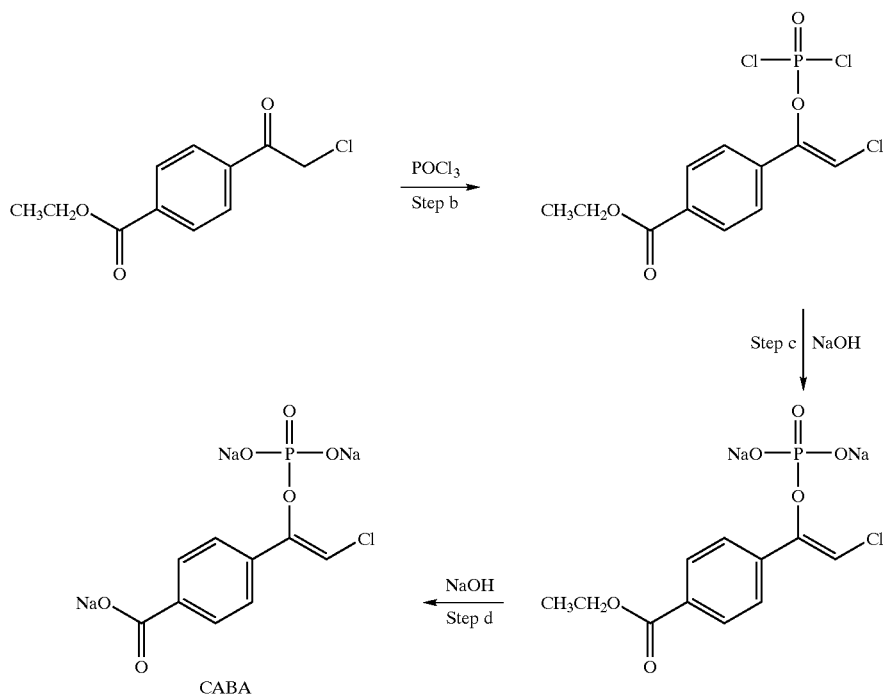

In one variation, the halogenating compound is sulfurylchloride. In other variations, the halogen is selected from the group consisting of Cl, Br and I. Thus, in one embodiment, the haloketone enol phosphate is BABA enol phosphate; in another embodiment, the haloketone enol phosphate is CABA enol phosphate.

The invention also discloses that, in a method for determining the amount of homocysteine in a sample wherein the homocysteine is modified by a reagent, the improvement comprises providing a precursor to the reagent and an enzyme capable of converting the precursor to the reagent. In one variation, the precursor is a protected alkylating reagent and the enzyme is capable of deprotecting the protected alkylating reagent. In another embodiment, the reagent is an α-haloketone and the precursor is an enol ester of the α-haloketone. One variation discloses that the enol ester is an enol phosphate and the enzyme is a phosphatase.

The present invention also discloses a method for releasing an alkylating reagent into an aqueous medium comprising combining, in an aqueous solution, an enol ether of an α-haloketone, an enol ester of an α-haloketone, an enol ether of an γ-halo-α,β-unsaturated ketone or an enol ester of an γ-halo-α,β-unsaturated ketone, and an enzyme capable of hydrolyzing the enol ether or ester.

In one variation, the enol ester is an enol phosphate and the enzyme is a phosphatase. In another embodiment, the aqueous solution further comprises a compound that becomes alkylated subsequent to the combining step.

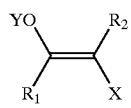

wherein $R_1$ and $R_2$ are alkyl, aryl or substituted alkyl or aryl; X is Cl, Br or I; and Y is a protecting group that may be removed by an enzyme.

In one embodiment, $R_1$ is —$C_6H_4COOH$, $R_2$ is H, X is Br and Y is —$PO_3H_2$. In another variation, $R_1$ is —$C_6H_4CONHZ$, $R_2$ is H, X is Cl and Y is —$PO_3H_2$. Another embodiment discloses that Z is H or $NH_2$. Alternatively, Z is selected from the group consisting of proteins, polypeptides, oligonucleotides, polysaccharides, and lipids. In one variation of the disclosed embodiment, the enzyme is alkaline phosphatase.

DETAILED DESCRIPTION

It has now been shown that α-haloketones can be protected by conversion to their corresponding enol phosphates. The enol phosphates are stable in aqueous solutions but can be rapidly converted to the free α-haloketone by addition of a phosphatase such as alkaline phosphatase. It is found possible to store the α-haloketone enol phosphates in the presence of nucleophilic reagents that would otherwise react with the unprotected α-haloketones. Before proceeding to a more detailed description of various embodiments of the present invention, however, it may be helpful to provide some useful definitions. The following are intended to be illustrative, and not limiting, of the present invention.

Definitions

As used herein, the term "analyte" refers to a compound or composition to be detected. The analyte can be a member of a specific binding pair ("sbp") and may be a ligand which is monovalent (monoepitopic) or polyvalent (polyepitopic), usually antigenic or haptenic, and is a single compound or plurality of compounds which share at least one common epitopic or determinant site.

This invention provides, among other aspects, compositions useful in a variety of methods for detecting an analyte in a sample that may also contain a homolog of the analyte, by chemically modifying the analyte and the homolog, then detecting the modified analyte. Therefore, the analyte is determined by detecting a reaction product whose presence will be detected only when the analyte of interest is present in the sample (i.e., the "modified" analyte is detected in the assay). The analyte can be found directly in a sample such as a body fluid from a host, for example, urine, blood, plasma, serum, saliva, semen, stool, sputum, cerebral spinal fluid, tears, mucus, or the like, but preferably is serum or plasma. The sample may be pretreated, as discussed below.

Member of a specific binding pair ("sbp" member): as used herein, these terms refer to one of two different molecules having an area on the surface or in a cavity that specifically binds to and is therefore defined as complementary with a particular spatial and polar organization of the other molecule. The members of the sbp can be referred to as ligand and receptor (or antiligand) such as members of an immunological pair, e.g., antigen-antibody, or they may be operator-repressor, nuclease-nucleotide, biotin-avidin, hormones-hormone receptors, nucleic acid duplexes, IgG-protein A, DNA-DNA, DNA-RNA, and the like.

As used herein, the term "ligand" refers to any compound for which a receptor naturally exists or can be prepared.

As used herein the term "receptors" refers to any compound or composition capable of recognizing a particular spatial and polar organization of a molecule, i.e., epitopic or determinant site. Complementary sbp members bind to one another, as for example, a ligand and its complementary receptor. Sbp members can be immunological pairs such as antigen and antibody, or non-immunological such as avidin and biotin or the complementary strands of an oligonucleotide. Sbp members can also be small molecules or residues of small molecules and their receptors. Illustrative receptors include naturally-occurring receptors (e.g., thyroxine binding globulin, antibodies, enzymes, Fab fragments, lectins, nucleic acids, repressors, protection enzymes, protein A, DNA binding proteins, and the like).

The terms "support," "matrix," or "solid phase" may be used interchangeably herein and are intended to mean any non-porous or porous surface that can have any one of a number of shapes, such as strip, rod, particle, slab, slide, beads of various shapes and contours, and the like. Typical support surfaces include glass or plastic beads, latex or cellulose particles, glass or cellulose filter paper, nitrocellulose membranes, polystyrene plates, magnetic particles, plastic tubes or vessels, and the like. The matrix may be of any convenient material to which a molecule can be non-diffusively bound and which does not dissolve in or react adversely with the ligand medium. Often, the support will be plastic such as polystyrene, polycarbonate, polyacrylate, polyvinylchloride, polyurethane, teflon and the like. Alternatively, the matrix may be metallic in nature, such as steel, nickel, copper, or gold. The support may also be made of a ceramic material including, for example, glass, quartz, and the like. When the support or matrix consists of beads, the beads are generally of a defined and approximately uniform size, preferably about 0.2 to 2.5 μm in diameter, and will have either a rough or smooth surface, depending on the application.

In many preferred embodiments, the surface is preferably smooth. preferably the beads are rounded or oblong, usually approximately spherical and have surface properties which minimize non-specific binding. As used in the assays of the present invention, the support will have bound to it a molecule—e.g., a ligand, a receptor, or more generally, a member of a specific binding pair. Suitable materials are known in the art and are described in, for example, Ullman, et al. U.S. Pat. No. 5,185,243 (see, e.g., columns 10–11); the disclosures of said patent are thus incorporated herein by reference. Similarly, the binding of sbp members to the support or surface may be accomplished by well-known techniques, commonly available in the literature. See, e.g., Chibata, "Immobilized Enzymes," Halsted Press, New York (1978) and Cuatrecasas, *J. Biol. Chem.* 245: 3059 (1970).

Depending upon the type of solid support used, it may also require pretreatment to provide for binding of a protein, ligand or receptor to its surface without interfering with the function of the protein, ligand or receptor. For example, avidin or streptavidin can be covalently bound to spherical glass beads of 0.5–1.5 μm and used to capture a biotinylated antibody.

As used herein, the terms "immunocomplex" or "immunecomplex" means the complex formed by the immunological binding of an antigen to an antibody.

Signal producing system ("sps"), as used herein, refers to one or more components, at least one component being a label, which generate a detectable signal that relates to the amount of bound and/or unbound label. Preferably, the label is a dye, fluorescer, radiolabel, enzyme, chemiluminescer or photosensitizer, which is detected by observing enzyme activity, luminescence, fluorescence, light absorbance, radioactivity, or some visual signal. A particularly useful system is one using photoactivated chemiluminescent labels, which is described in greater detail in Section C below—but it should be appreciated that the invention is not limited to the exemplary systems described herein.

Suitable labels include, by way of illustration and not limitation, enzymes such as alkaline phosphatase and horseradish peroxidase; a substrate for a replicase such as QB replicase; promoters; dyes; fluorescers, such as fluorescein, rhodamine compounds, phycoerythrin, phycocyanin, allophycocyanin, o-phthaldehyde, and fluorescamine; chemiluminescers such as isoluminol; sensitizers; coenzymes; enzyme substrates; radiolabels such as $^{125}$I, $^{131}$I, $^{14}$C, $^{3}$H, $^{32}$P and $^{35}$S; particles such as latex or carbon particles; metal sol; crystallite; liposomes; cells, etc., which may or may not be further labeled with a dye, catalyst or other detectable group and the like. Suitable enzymes and coenzymes are disclosed in Litman, et al., U.S. Pat. No. 4,275,149, columns 19 to 28, and Boguslaski, et al., U.S. Pat. No. 4,318,980, columns 10 to 14; suitable fluorescers and chemiluminescers are disclosed in Litman, et al., U.S. Pat. No. 4,275,149, at columns 30 and 31. Particularly useful photoactivated chemiluminescent labels and methods for their preparation and use are disclosed in U.S. Pat. No. 5,340,716 to Ullman et al. (The disclosures of the foregoing are all incorporated by reference herein.)

The term "particles" as used herein, refers to particles of at least about 20 nm and not more than about 20 microns, usually at least about 40 nm and less than about 10 microns, preferably from about 0.10 to 2.0 microns diameter, normally having a volume of less than 1 picoliter. Particles may be organic or inorganic, swellable or non-swellable, porous or non-porous, having any density, but preferably of a density approximating water, generally from about 0.7 to about 1.5 g/ml, preferably suspendable in water, and composed of material that can be transparent, partially transparent, or opaque. The particles may or may not have a charge, and when they are charged, they are preferably negative. Particles may be solid (e.g., polymer, metal, glass, organic and inorganic such as minerals, salts and diatoms), oil droplets (e.g., hydrocarbon, fluorocarbon, silicon fluid), or vesicles (e.g., synthetic such as phospholipid or natural such as cells and organelles). The particles may comprise latex or other synthetic or natural materials, including organic or inorganic polymers; lipid bilayers (e.g., liposomes, phospholipid and non-phospholipid vesicles); oil droplets; silicon particles; metal sols; cells; and dye crystallites.

Organic particles will normally include polymers, either addition or condensation polymers, which are readily dispersible in the assay medium. The organic particles are also preferably adsorptive or functionalizable as to bind at their surface, either directly or indirectly, an sbp member and to bind at their surface or incorporate within their volume a dye such as a fluorescer, a photosensitizer or a photochemically activatable chemiluminescent compound.

The particles can be derived from naturally occurring materials, naturally occurring materials which are synthetically modified, and synthetic materials. Natural or synthetic assemblies are preferred. Among organic polymers of particular interest are polysaccharides, particularly cross-linked polysaccharides, such as agarose (which is available as SEPHAROSE), dextran (available as SEPHADEX and SEPHACRYL), cellulose, starch, and the like; addition polymers, such as polystyrene, polyacrylamide, homopolymers and copolymers of derivatives of acrylate and methacrylate, particularly esters and amides having free hydroxyl functionalities including hydrogels, and the like. Inorganic polymers include silicones, glasses, available as Bioglas, and the like. Sols include gold, selenium, and other metals. Particles may also be dispersed water insoluble dyes such as porphyrins, phthalocyanines, etc., which may also act as photosensitizers. Particles may also include diatoms, cells, viral particles, magnetosomes, cell nuclei and the like. Where the particles are commercially available, the particle size may be varied by breaking larger particles into smaller particles by mechanical means, such as grinding, sonication, agitation, etc.

The particles will usually be polyfunctional or be capable of being polyfunctionalized or be capable of being bound to an sbp member, photosensitizer, or photochemically activatable chemiluminescent compound through specific or non-specific covalent or non-covalent interactions. A wide variety of functional groups are available or can be incorporated. Exemplary functional groups include carboxylic acids, aldehydes, amino groups, cyano groups, ethylene groups, hydroxyl groups, mercapto groups and the like. When covalent attachment of a sbp member, chemiluminescent compound or photosensitizer to the particle is employed, the manner of linking is well known and is amply illustrated in the literature. See for example Cuatrecasas, *J. Biol. Chem.* 245: 3059 (1970). The length of a linking group may vary widely, depending upon the nature of the compound being linked, the nature of the particle, the effect of the distance between the compound being linked and the particle on the binding of sbp members and the analyte and the like.

Particles and other matrix materials may also be tagged with labeling means. For example, U.S. Pat. No. 5,709,994 (the disclosures of which are incorporated by reference herein) describes methods of preparing particles tagged with photosensitizer and/or chemiluminescence and/or energy acceptor compounds. (See, e.g., examples 1–2 of U.S. Pat. No. 5,709,994.)

There are numerous methods by which the label can produce a signal detectable by external means, such as visual examination, electromagnetic radiation, electrochemical detection, photoacoustic spectroscopy, and the like. The label or other sps members can also be bound to an sbp member, another molecule or to a support. The label can directly produce a signal, and therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. Other labels that directly produce a signal include radioactive isotopes and dyes.

Alternately, the label may need other components to produce a signal, and the sps would then include all the components required to produce a measurable signal, which may include substrates, coenzymes, enhancers, additional enzymes, substances that react with enzymatic products, catalysts, activators, cofactors, inhibitors, scavengers, metal ions, specific binding substance required for binding of signal generating substances, and the like. A detailed discussion of suitable signal producing systems can be found in Ullman, et al. U.S. Pat. No. 5,185,243, columns 11–13, which is incorporated herein by reference.

The label can be bound covalently to numerous sbp members: an antibody that binds the modified analyte; a receptor for an antibody that binds the modified analyte; a receptor that is capable of binding to a small molecule conjugated to an antibody that binds the modified analyte; or a ligand, particularly an analog of the modified analyte. Bonding of the label to the sbp member may be accomplished by chemical reactions which result in replacing a hydrogen atom of the label with a bond to the sbp member or may include a linking group between the label and the sbp member. Other sps members may also be bound covalently to sbp members. For example, two sps members such as a fluorescer and quencher can be bound respectively to an analog of the modified analyte and an antibody to the analyte that forms a complex with the analog. Formation of the complex brings the fluorescer and quencher in close proximity, thus permitting the quencher to interact with the fluorescer to quench the signal.

Methods of conjugation are well known in the art. See for example, Rubenstein, et al., U.S. Pat. No. 3,817,837, which is incorporated herein by reference. This invention also contemplates having an antibody bound to a first member of a signal producing system and a detectable label as the second member of a signal producing system. For example, when the detectable label is bound to an analyte analog, the extent of binding of the antibody to the analog can be measured by detecting the signal produced by the interaction of the signal producing system members.

Ancillary Materials: various an cillary materials will frequently be employed in the methods in accordance with the present invention. For example, buffers will normally be present in the assay medium, as well as stabilizers for the assay medium and the assay components. Frequently, in addition to these additives, proteins may be included, such as albumins, organic solvents such as formamide, quaternary ammonium salts, polycations such as dextran sulfate, or surfactants, particularly non-ionic surfactants, binding enhancers, e.g., polyalkylene glycols, or the like.

As used herein, the term alkylating reagents includes α-haloketones, α-haloaldehydes, γ-halo-α,β-unsaturated ketones, and γ-halo-α,β-unsaturated α-haloaldehydes. These reagents are capable of reacting with sulfhydryl, amino, and hydroxyl groups. Alkylating reagents used for homocystein (hcy) react with the sulfhydryl group of hcy. Alkylating reagents of the present invention may also have the formula $YR_1C\!\!-\!\!(CR_3\!\!=\!\!CR_4)_n\!\!-\!\!COR_2$, where $R_1$, $R_2$, $R_3$ or $R_4$ can be independently hydrogen (H), alkyl, or aryl and taken together to form rings; n=0 or 1; and Y=Cl, Br or I.

As used herein, alkyl refers to a monovalent branched or unbranched radical derived from an aliphatic hydrocarbon by removal of one H atom; includes both lower alkyl and upper alkyl.

Lower alkyl, as used herein, refers to alkyl containing from 1 to 5 carbon atoms such as, e.g., methyl, ethyl, propyl, butyl, isopropyl, isobutyl, pentyl, isopentyl, etc.

Upper alkyl, as used herein, refers to alkyl containing more than 6 carbon atoms, usually 6 to 20 carbon atoms, such as, e.g., hexyl, heptyl, octyl, etc.

As used herein, aryl refers to an organic radical derived from an aromatic hydrocarbon by the removal of one atom and containing one or more aromatic rings, usually one to four aromatic rings, such as, e.g., phenyl (from benzene), naphthyl (from naphthalene), etc.

As used herein, aralkyl refers to an organic radical having an alkyl group to which is attached an aryl group, e.g., benzyl, phenethyl, 3-phenylpropyl, 1-naphthylethyl, etc.

The term substituted, as used herein, means that a hydrogen atom of a molecule has been replaced by another atom, which may be a single atom such as a halogen, etc., or part of a group of atoms forming a functionality such as a substituent having from 1 to 500 atoms (other than the requisite hydrogen atoms necessary to satisfy the valencies of such atoms), which atoms are independently selected from the group consisting of carbon, oxygen, nitrogen, sulfur and phosphorus, and which may or may not be bound to one or more metal atoms.

"Small molecules," which may alternatively be identified herein as small organic molecules (i.e. if they include organic or organometallic groups), analytes, or haptens, tend to have a molecular weight of less than about 2,000, more preferably up to about 1,500, and even more preferably up to about 1,000. In various preferred embodiments, small molecules have a molecular weight of at least about 100, more preferably 200 or more, and even more preferably 250 or more.

Many of the small molecules useful as disclosed herein have a molecular weight of from 100 to 2000, preferably 150 to 1000, and specific receptors for the corresponding small molecule either exist or can be prepared. Examples of small molecules include derivatives of biotin, lysergic acid, fluorescein or a fluorescein derivative, and vitamin $B_{12}$, with the corresponding receptors being avidin or streptavidin, anti-lysergic acid, anti-fluorescein and intrinsic factor, respectively. Antibodies to small molecules can be prepared by linking the small molecule to an immunogenic carrier. The term "small molecules," as used herein, encompasses drugs, metabolites, pesticides, pollutants, and the like as described and exemplified in U.S. Pat. Nos. 5,340,716 and 5,709,994, for example, the disclosures of which are incorporated herein by reference.

The term "polymers," alternatively identified herein as "large molecules" or "high molecular weight (HMW) molecules," includes a variety of molecules including proteins, oligonucleotides, lipids, carbohydrates, lipopolysaccharides, glycoproteins, and the like. Polymers such as receptor analytes may have molecular weights generally ranging from about 10,000 to $2\times10^8$, more usually from about 10,000 to $10^6$. For immunoglobulins, such as IgA, IgG, IgE and IgM, the molecular weights generally vary from about 160,000 to about $10^6$. Enzymes generally range from about 10,000 to 1,000,000 in molecular weight, although it is not inconceivable for an enzyme to have a weight of less than 10,000 or greater than 1,000,000. Natural receptors and binding molecules vary widely in molecular weight, as do their synthetic versions and mimics, although they generally range from about 25,000 to $10^6$ and higher. Receptors/binding molecules such as avidin, DNA, RNA, thyroxine binding globulin, thyroxine binding prealbumin, transcortin, lectins, protein A, complement components, and the like are but a few examples of such HMW molecules.

Protected alkylating reagents useful for coupling two molecules in aqueous solutions must have a group suitable for conjugating the reagent to one of the molecules of interest. The other molecule must have a nucleophilic group such as OH, SH or amine or be modified to include such a group. The two molecules are coupled by combining the molecule conjugated to the reagent, the molecule with a nucleophilic group and an activating agent.

"Activating reagent," as used herein, refers to a catalyst, usually a biocatalyst, preferably an enzyme, ribozyme or catalytic antibody. In various embodiments, preferred activating reagents include enzymes such as hydrolases, including phosphatases, phosphodiesterases, glycosidases and other esterases.

Examples of protected alkylating reagents which are consistent with the following formula

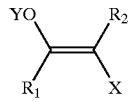

are illustrated below. The activating reagents or enzymes useful in the deprotection of such protected alkylating reagents are also listed in the following chart.

| $R_2$ | $R_1$ | X | Y | Activating Reagent (Enzyme) |
|---|---|---|---|---|
| H | —$C_6H_4COOH$ | Br | —$PO_3H_2$ | alkaline phosphatase |
| H | —$C_6H_4CONHZ^*$ | Cl | —$PO_3H_2$ | alkaline phosphatase |

-continued

| R$_2$ | R$_1$ | X | Y | Activating Reagent (Enzyme) |
|---|---|---|---|---|
| H | —CH$_2$CH$_2$OZ | I | 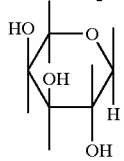 | β-galactosidase |
| C$_6$H$_5$ | —CH$_2$N+(CH$_3$)$_3$ | Cl | —COCH$_3$ | acetyl cholinesterase |
| H | —COOH | Br | —SO$_3$H | sulfatase |
| —CH$_2$CH$_2$CH$_2$— (R$_1$ and R$_2$ form a ring)** | | I | —CON(CH$_3$)$_2$ | catalytic monoclonal antibody |

*Z=H or an organic molecule or NH$_2$. Z may be a biopolymer such as a protein, polypeptide, nucleic acid, oligonucleotide, polysaccharide, etc.
**Not possible unless X and R2 exchange positions, i.e.,

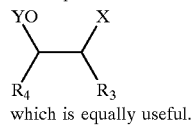

which is equally useful.

DETAILED DESCRIPTION
A. Preparation of Protected Reagents

As noted previously, a number of protecting groups are useful in the preparation of protected reagents for use according to the present invention. For example, suitable protecting groups include esters or ethers of carboxylates, carbohydrates, nucleic acids, lipids, phosphates, and the like. Enzymes useful in removing such protecting groups thus include esterases, glycosidases, nucleases, ribozymes, lipases, hydroxylases, and phosphatases.

For a useful protecting group, one may utilize an ester, preferably one which can be easily removed under mild conditions—e.g., via the use of an enzyme. Exemplary ester protecting groups include formate, benzoyl formate, acetate, substituted acetate, propionate, isobutyrate, levulinate, crotonate, benzoate, napthoate and many other esters. (See, e.g., Greene, T. W., *Protective Groups in Organic Chemistry*, John Wiley & Sons, New York, 1981.) Similarly, a wide variety of carbohydrates, from simple sugars to polysacharides, can be used as protecting groups that are specifically removable via the use of an appropriate enzyme. As those of skill in the art will appreciate, modified protecting group molecules—e.g., molecules that comprise esters, carbohydrates, etc. as well as other moieties—may also be used as protecting groups within the context of the present invention.

Thus, it should be understood that while phosphate groups are described as exemplary protecting groups herein, they are precisely that: examples of molecules that are useful within the context of this invention. In one variation of the present invention, enol-phosphate derivatives of BABA and CABA have been found to be particularly useful in various applications, including the conjugation of small and large molecules and the detection of various analytes in assay contexts. One example of the latter is an assay for homocysteine (hcy).

For example, BABA is often used as an alkylating reagent for the differentiation and antibody recognition of serum and plasma homocysteine. Homocysteine is a marker for nutritional assessment, cardiovascular risk and neonatal homocysteinuria. BABA-phosphate, a "pro-BABA," has several advantages over BABA. BABA has limited stability when stored above physiological pH and limited solubility at lower pH. BABA-phosphate has significantly increased stability at higher pH and increased solubility over a broad pH range. It has the added advantage of potential compatibility with reagents in a two-component system. CABA phosphate behaves similarly and is easier to prepare. CABA-phosphate and BABA-phosphate are readily deprotected by alkaline phosphatase.

The chemical structure of BABA and that of the phosphate-protected form of its close relative, CABA, is illustrated below. Substitution of Cl for Br in the first structure will produce the structure for CABA; similarly, substitution of Br for Cl in the second structure produces the structure for BABA-phosphate.

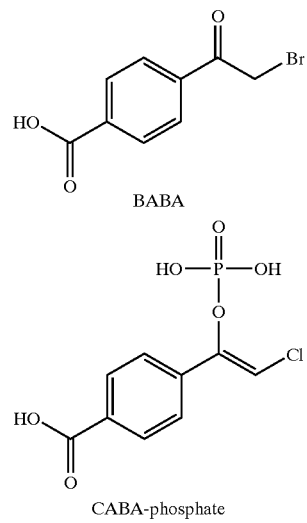

CABA and BABA alkylate the sulfhydryl groups of cysteine (cys) and homocysteine. The amino group of the alkylated cysteine but not the alkylated homocysteine reacts internally with the ketone introduced by CABA or BABA to give a cyclic structure. Methods of preparing BABA and CABA are available in the art; see, e.g., U.S. Pat. No. 5,478,729 (e.g., columns 21–22), the relevant disclosures of which are incorporated by reference herein.

Because antibodies to the alkylated homocysteine (hcy-ABA) can differentiate hcy-ABA from the cyclic alkylated cysteine (cys-ABA), an immunoassay for hcy using these antibodies will give accurate results even in the presence of cysteine. By contrast, an immunoassay for hcy without prior alkylation and using antibodies to hcy cannot differentiate between these two homologous amino acids.

BABA and CABA incorporate a variety of designed functionalities that are important to retain. For example, the following functionalities are important: 1) the haloacetyl group has a fast reaction rate with thiols; 2) the phenyl ring can provide a highly immunogenic moiety when presented to an immune system; 3) the carboxylate provides some degree of water solubility as well as a convenient point of attachment to a carrier protein for preparation of an immunogen; and 4) the carbonyl of the haloacetyl group provides a convenient means of differentiating between the cysteine and homocysteine adducts.

In order to retain all of the foregoing features, while providing increased stability and solubility, protected forms of BABA and CABA (e.g., "pro-BABA" and "pro-CABA") are aspects of the present invention. The use of enol-phosphate derivatives of BABA and CABA (pro-BABA and pro-CABA) provide these benefits and these derivatives can readily be deprotected by alkaline phosphatase to afford BABA or CABA during the process of carrying out an assay.

The use of pro-BABA or pro-CABA provides, as a further advantage, the ability to combine reagents that would otherwise be incompatible and thus permit assays to be performed with fewer addition steps. For example, an assay with unprotected BABA requires mixing the sample with a releasing reagent to reduce hcy disulfides. BABA is then added together with an antigen reagent and an antibody reagent. When pro-BABA or pro-CABA is used, the releasing agent and pro-BABA or pro-CABA can be combined with the antigen as a first reagent and alkaline phosphatase can be combined with the antibody as a second reagent, thereby reducing the number of assay reagents from three to two.

Though enol-phosphates have been reported to be difficult to synthesize (see, e.g., Kearney and Valentino, Pharm. Res. 9: 3789 (1992)), we have been able to prepare them with great success. For example, CABA-phosphate is successfully prepared on a 40 gram scale in good overall yield. Referring to the synthetic scheme (see Scheme A) below; numbers in bold type in text correspond with the structures shown in the Scheme), commercially available ethyl 4-acetylbenzoate (1, 197 mmol) is selectively monochlorinated (see, e.g., Rogic et al., *J. Org. Chem.* 46: 4486–9 (1981)) in 78% yield affording 99% pure product (as determined using nuclear magnetic resonance (NMR) analysis; see Scheme A). When bromination is used in order to obtain the vinyl bromide enol-phosphate analog of BABA, partial to complete displacement of the bromine with chloride occurred during the phosphorylation step. The chloro derivative proved to be as effective as the bromo derivative in assays using photoactivated chemiluminescent labels. The synthesis based on the chloro derivative is cleaner and more reproducible.

1. Materials

All reagents are reagent grade and are used without further purification with the exception of THF which is freshly distilled from sodium before use and diisopropylethylamine which is dried over 3 Å sieves. Silica gel 250 analytical plates are obtained from Analtech (Newark, Del.). $^1$H-NMR is recorded on a Bruker 250 MHz FT-NMR Spectrometer using deuterated solvents obtained from Aldrich (Milwaukee, Wis.). UV spectra are run on a Hewlett Packard model 8452A Diode Array Spectrophotometer. All reactions are run under an argon atmosphere. Elemental analysis, mass spectra, and NMR spectra ($^1$H, $^{31}$P) are performed in-house or via commercial entities—e.g., Berkeley Labs.

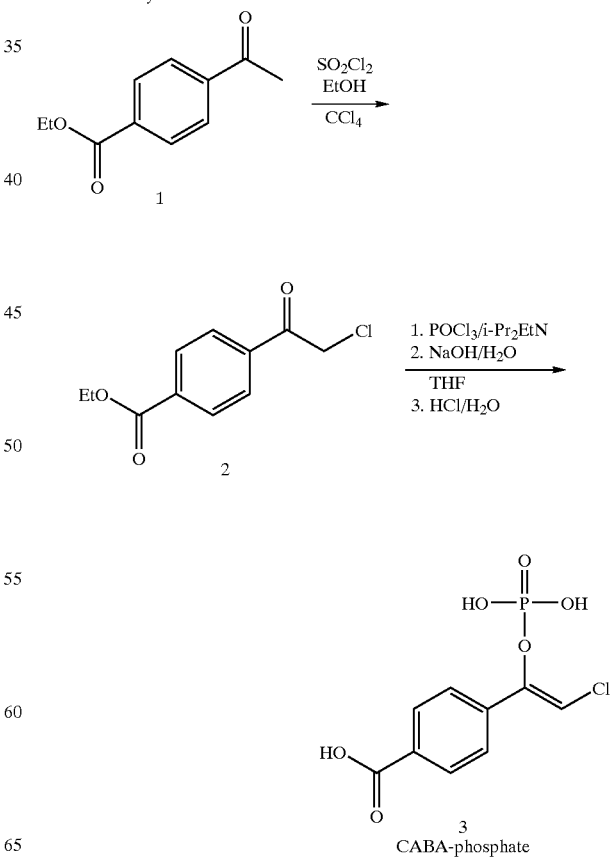

Scheme - A: Synthesis

Scheme - B: Assay

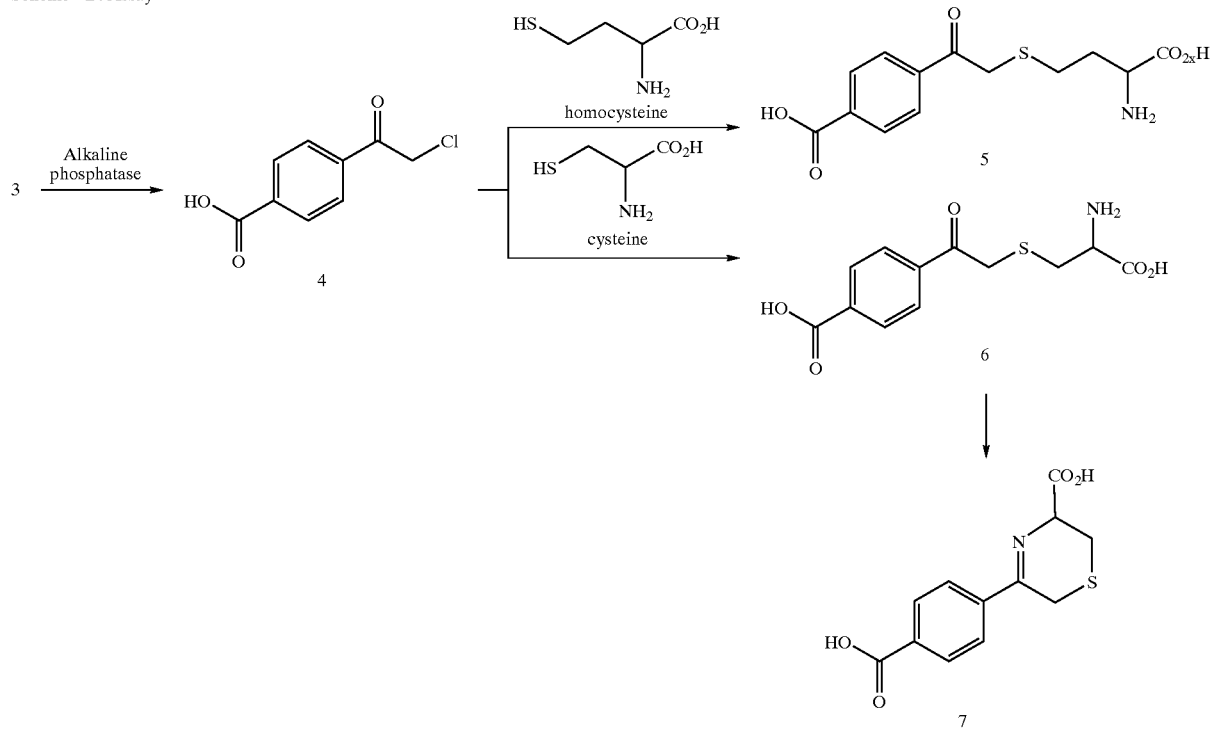

2. Synthesis (See Synthetic—Scheme A)

a. Preparation of Ethyl-4-(chloroacetyl)benzoate (2)

Ethyl 4-acetylbenzoate (Aldrich 99%, 37.87 g, 197 mmol) is dissolved in 350 mL $CCl_4$ to which 11.3 mL (197 mmol) anhydrous ethanol is added. A solution of sulfuryl chloride (20 mL, 236 mmol) in 50 mL $CCl_4$ is added dropwise over 20 min. After 30 min when effervescence had ceased, the reaction is checked by NMR and thin-layer chromatography (TLC). (The substitution ratio by NMR is as follows: 2% dichloro: 74% monochloro: 24% (1). Further heating for 20 min at 50° C. did not change the ratio. TLC: 5×20 $SiO_2$: (1:3) 4% $MeOH/CH_2CL_2$-hexane).

Six (6.0) mL (71 mmol) more sulfuryl chloride in 20 mL $CCl_4$ is added dropwise. After 20 minutes, effervescence cease. (The NMR ratio is: 7.5% dichloro: 92% monochloro: 0.5% (1).) After an additional 15 min, the reaction is slowly poured into 500 mL well stirred saturated aqueous $NaHCO_3$ and rinsed with 100 mL $CH_2Cl_2$ (to prevent premature crystallization). The reaction is stirred until effervescence ceased (pH=8). The phases are separated, and the organic phase is washed once with 500 mL water, dried with $Na_2SO_4$ and concentrated to dryness.

The solid is redissolved in 200 mL anhydrous ethanol at 80°. (The NMR ratio of the worked up product before crystallization is: 8.0% dichloro; 92% monochloro: 0.0% (1, Scheme A).) After crystallizing for 3 hours at ambient temperature, the product is filtered, washed with 50 mL freezer-cooled ethanol, and dried (0.1 mmHg) yielding a 25.5 g first crop. The filtrate is concentrated to about 100 mL and cooled for 2 h in the freezer. The second crop is washed twice with 25 mL portions of freezer cooled ethanol, and dried (0.1 mmHg, 7.4 g).

The combined crops (99% pure monochloro product by NMR) are used directly in the next step. A third crop (1.9 g, pure by TLC) is also collected. The combined yield of the three crops (34.8 g, 154 mmol) is 78%.

b. Preparation of 4-(chloroacetyl)benzoate enol-phosphate sodium salt (3, Scheme A) (CABA-phosphate)

The ethyl-4-(chloroacetyl)benzoate (2, Scheme A) (32.15 g, 141.8 mmol) is dissolved in 400 mL THF. Diisopropyl-ethylamine (86 mL, 496 mmol) is added to the clear colorless solution. The resulting clear pale greenish-yellow solution is bubbled with argon for two min. and stirred in an ice bath until the internal temperature is less than 10° C. The $POCl_3$ (33 mL, 355 mmol) dissolved in 50 mL THF is added dropwise at such a rate that the temperature does not exceed 10° C. (1.5 hr). The reaction is allowed to warm to ambient temperature overnight. The white crystals (amine hydrochloride salts) are removed by filtration and washed with 100 mL THF into the filtrate. (The crystals are dried and weighed. The weight (18.71 g) of pure amine-HCl salt is used to adjust the calculation for the amount of NaOH to add at the hydrolysis step.)

The clear orange filtrate is added dropwise to 720 mL ice bath-cooled argon purged 2.50 $\underline{N}$ aqueous NaOH (1800 mmol) at such a rate that the reaction temperature does not exceed 15° C. (1.5 h). (The amount of NaOH is based on 5×355 mmol $POCl_3$ used +142 mmol ester to hydrolyze −113 mmol amine-HCl salts removed by filtration.) The reaction is allowed to warm to ambient temperature overnight. The inorganic salts removed by filtration are washed twice with 100 mL portions of THF into the filtrate. (These salts contain only trace amounts of product by UV comparison with a standard.) The two-phase filtrate is separated and the aqueous phase is extracted twice with 150 mL portions of THF. The combined THF phase is discarded. (This organic phase is calculated to contain less than 1 g product by NMR analysis of the concentrated solid.)

The aqueous phase is adjusted from pH 10.9 to pH 12.5 with 25 mL 2.5 $\underline{N}$ NaOH and the solution is stirred overnight to hydrolyze remaining ester (the amount of unhydrolyzed ester is estimated to be 24% by NMR). The pale yellow solution (pH 11.8) is concentrated to dryness at 40° C. removing traces of remaining organic solvents and diisopropylethylamine. The residue (110 g) is redissolved in 170 mL water at 50° C., cooled to ambient temperature and the pH is adjusted to 3.0 with 90 mL 3 N HCl added dropwise. The creamy white suspension is refrigerated for 2 h, and filtered. The filter cake is washed twice with 100 mL portions of ice water and dried to constant weight (0.1 mmHg). At this pH the precipitate is still quite water soluble, thus the amount of water used must be kept at a minimum. In an examplary prep, the dried, powdery-white product weighed 40.7 g. The practical formula weight is calculated to be 351 mg/mmol by 250 MHz $^1$H-NMR using an internal standard (described in the following two paragraphs) which corresponds well with the value (360 mg/mmol) obtained from elemental analysis.

Dioxane (10.0 μl/10.00 mL D$_2$O, 0.00822 mmol/0.70 mL NMR solution, 8 $^1$H s 3.7, 1.954 integration units) is used as the internal standard. The CABA-phosphate (25.4 mg/0.70 mL NMR solution) vinyl proton E/Z isomer integration units ($^1$H d 6.5, 2.152 integration units) are added together. (When de-phosphorylated under assay conditions, both isomers give the same product).

Calculation:

8×2.15 vinyl $^1$H×0.00822=0.0724 mmol CABA-phosphate 1.954 dioxane $^1$H 25.4 mg/0.0724 mmol=351 mg/mmol The formula weight of fully protonated CABA-phosphate is 278 mg/mmol. The practical formula weight takes into account the weight of sodium counter-ions in the product, water of hydration and residual sodium chloride. Using this formula weight, 40.7 g represents 116 mmol CABA-phosphate or a yield of about 82%.

The product is also analyzed by 400 MHz $^1$H and $^{31}$P NMR for the ratio of E/Z isomers and purity as organic phosphate (data not shown). Mass spectra shows the parent ion (277 M-1) and (299 M-2+Na) in the negative ion mode. Elemental analysis (theory %: C, 30.00; H, 3.08; Cl, 14.39; P, 8.61; Na, 8.69. found %: C, 30.04; H, 2.93; Cl, 14.36; P, 8.62; Na, 8.64) is consistent with the dihydrate of the mono sodium salt of CABA-phosphate, containing 7.5% by weight NaCl. Calculations based on the elemental analysis of this batch are consistent with a 0.9 eg Na+ counter-ion, 2 eq water of hydration, and 7.5% NaCl. The percent residual sodium chloride can be further reduced by additional cold water washes of the precipitated product with a concomitant loss in product yield.

c. Preparation of 2-Halovinylglycosides

Halovinylglucosides and other halovinylglycosides are useful alternatives to halovinylphosphates in the present invention. Enzymatic hydrolysis releases 2-chloroacetaldehyde with undergoes the same cyclization reaction with cysteine as the phenacyl chloride used in various examples herein. For example, a particularly preferred compound is 2-chlorovinyl-β-galactoside. β-galactosides are desirable because of the commercial availability of β-galactosidase, its high catalytic activity, and its good stability.

The preparation of vinyl glucosides from acylated sugars and ethoxyethylene and its enzymatic hydrolysis to give acetaldehyde is described in Heisei, JP 05039241 or Kitazawa et al., *Chem. Lett.* 6: 569–72 (1975), the disclosures of which are incorporated by reference herein. Using a similar procedure, 2-halovinylglycosides may be prepared using 1-chloro-2-ethoxyethylene in place of ethoxyethylene.

The usefulness of various glycosides—e.g., vinyl glycosides and 1-ethoxyethyl glycosides—as substrates for glycosidases is described in Dettinger et al., *Carbohydr. Res.* 87(1): 63–70 (1980), the disclosures of which are incorporated by reference herein. Thus, the present invention further provides for the use of halovinylglucosides and other halovinylglycosides as useful alternatives to halovinylphosphates. Enzymatic hydrolysis releases 2-haloacetaldehyde which is expected to undergo the same cyclization reaction with cysteine as the phenacyl chloride used in assays such as those described in the Examples below.

B. Exemplary Assay Methods

1. General Overview

Appropriate reaction conditions are chosen for carrying out the methods in accordance with the present invention. The following description sets forth suitable conditions, which are subject to modification by those skilled in the art depending on the specific reagents and assay protocol chosen for any particular application. For example, the methods of this invention can be applied to numerous types of assays such as heterogeneous, homogeneous, competitive or direct assays, and the conditions and reagents used will be selected accordingly.

The sample, preferably in a suitable medium, can be examined directly or may be pretreated before the sample is added to the assay medium. Pretreatment can render the analyte more readily available to one or more of the assay reagents or more readily detectable by reducing interference in the assay by removing any unwanted materials. The sample may be pretreated to separate or lyse cells; to precipitate, hydrolyze or denature proteins; to hydrolyze lipids; to solubilize the analyte; and the like. Such pretreatment may include, without limitation: centrifugation; treatment of the sample with an organic solvent (for example, an alcohol, preferably an alcohol having less than about 7 carbon atoms such as methanol); treatment with detergents; and treatment with releasing agents which may include reducing agents.

The concentration of the compound to be assayed will generally vary from about $10^{-4}$ to $10^{-15}$ M, more usually from about $10^{-5}$ to $10^{-12}$ M. More specifically, for an hcy analyte, the concentration will generally vary from about $10^{-4}$ to $10^{-8}$ M, more usually from about $10^{-5}$ to $10^{-7}$ M. Considerations such as whether the assay is qualitative, semi-quantitative or quantitative, the particular detection technique, and the concentration of the analyte will normally determine the concentration of the other reagents. In addition, the final concentration of each of the reagents will normally be determined empirically to optimize the sensitivity of the assay over the range of interest.

The relative amounts of the various reagents used in the assay and packaged in the kits described below can be varied, widely to provide for concentrations of the reagents that substantially optimize the reactions that need to occur during the present method and to further substantially optimize the sensitivity of any assay performed. The concentration of the antibodies in the assay medium is dependent on the type of assay (e.g., heterogeneous or homogeneous, competitive or direct, etc.). Normally, the anti-modified analyte antibody will be present in the assay medium in a concentration of about half to $10^7$ times the concentration of the modified analyte, more usually from about equal to about $10^3$ times the concentration of the modified analyte.

In carrying out the methods of this invention, preferably an aqueous medium will be employed. Other polar cosolvents may also be employed in the medium, usually oxygenated organic solvents of from 1–6, more usually from 1–4, carbon atoms, including alcohols, ethers and the like. Usually these cosolvents will be present in an amount less than about 70 weight percent, and more often, in less than about 30 weight percent.

In assays in accordance with the present invention, the pH for the medium will usually be in the range of about 5–10, with the range of about 7–9 being somewhat more preferred. The pH is chosen so as to maintain a significant level of binding between sbp members while optimizing signal producing proficiency. In some instances, a compromise will be made between these two considerations. In addition, the pH may also be selected so as to maintain a particular structural conformation such as cyclization. Various buffers may be used to achieve the desired pH and maintain the pH during the determination. Illustrative buffers include borate, phosphate, carbonate, Tris, barbital and the like. The particular buffer employed is not critical to this invention but in individual assays, one buffer may be preferred over another.

Moderate temperatures are normally employed for carrying out the methods of the present invention. The temperature may vary with the step being undertaken. More typically, however, a constant temperature is maintained during the relevant time period. The temperatures will generally range from about 10° to about 50° C., usually from about 15° to about 40° C.

While the order of addition of the various reagents may be varied widely, there will be certain preferences depending on the nature of the particular assay format being used. The reagents and sample can be combined simultaneously or wholly or partially sequentially with each other and the support. As used herein, the term "wholly or partially sequentially" means that, when the sample and various reagents utilized in the present invention are combined other than concomitantly (simultaneously), one or more of the reagents may subsequently be added alone, or together with other reagents. For example, a sample suspected of containing the analyte and the reducing agent may be combined first to allow the reduction of any disulfide bonds, followed by the simultaneous or stepwise addition of the remaining reagents.

Optionally, one or more incubation steps may be involved after each reagent addition, generally ranging from about 30 seconds to 6 hours, more usually from about 2 minutes to 1 hour. It is understood that there are certain sequences of steps that are more convenient and the choice of the particular sequence to be employed depends upon the selection of reagents and assay format and is not critical to the invention.

The final step of an immunoassay is to measure the extent of binding between the modified analyte and the antibody, which is related to the presence or amount of the analyte in the sample. There are numerous ways to measure the extent of binding which are well known in the art. These methods tend to differ depending on the nature of the assay—i.e. whether the assay is competitive, homogeneous, heterogeneous, and so forth.

One measurement of the extent of binding between the modified analyte and the antibody can be accomplished by adding detectably labeled modified analyte, i.e., a labeled analyte analog, and detecting the signal produced by binding of the labeled modified analyte with the antibody in competition with binding of the modified analyte. For example, in a homogeneous assay, the detectable label can be an enzyme and the final step might involve activating the enzyme label by addition of substrate. The signal produced is related to the extent of binding between the labeled modified analyte and the antibody. The presence or amount of signal is then related to the presence or amount of analyte in the sample.

In another measurement in a competitive, homogeneous assay, the extent of binding can be determined by use of a fluorescer-labeled modified analyte and a quencher-labeled antibody. The signal is again related to the extent of binding and which in turn is inversely related to the amount of analyte present in the sample. Alternatively, a homogeneous non-competitive assay may be used in which the fluorescer-labeled modified analyte is not added as a separate reagent but is formed by reaction of the analyte with a fluorescer-labeled modifying reagent. In this case, the signal is again related to the extent of binding, which is directly related to the amount of analyte present in the sample.

In a heterogeneous assay, unlabeled anti-(modified analyte) antibodies may be bound to a support. Following incubation of the support with the modified analyte and labeled modified analyte, the support is separated from the liquid phase and the amount of signal from the solid phase or the liquid phase is then determined. This indicates the extent of binding between the modified analyte and the antibody, and thus the amount of analyte in the sample. For a more detailed discussion of the above immunoassay techniques, as well as other exemplary techniques useful as disclosed herein, see Maggio, Edward T., "Enzyme-Immunoassay," CRC Press, Inc., Boca Raton, Fla., 1980.

2. Example: hcy Assay

For illustrative purposes, the following assay protocols can be utilized. These illustrations should not be construed as limiting the scope of the invention, however; they are merely illustrative of the qualitative, semi-quantitative and quantitative assay protocols in which the methods of this invention can be used for determining hcy or cys in a sample. The signal detected in these methods is compared to a standard or control having a known concentration of hcy.

In an assay for hcy using alkylating reagent, a monoclonal antibody that specifically binds to modified Hcy—and not to modified cys,—is preferred for use. A sample suspected of containing hcy and cys is combined with protected alkylating reagent in a suitable medium. Upon addition of an activating reagent, the protected alkylating reagent will be deprotected and the reactions will occur as follows: Alkylating Reagent+hcy→modified hcy and Alkylating Reagent+cys→modified cys, if hcy and cys are present. An analog of modified hcy, conjugated to glucose-6-phosphate dehydrogenase and the anti-modified hcy antibody are also added to the medium. Binding of the anti-modified hcy antibody to the modified hcy conjugated to G6PDH results in inhibition of the enzyme. After incubation for 30 minutes, glucose-6-phosphate is added. The signal produced is directly related to the amount of hcy in the sample.

As noted previously, in a sample assay, a monoclonal antibody specific for modified hcy (and not modified cys), is preferably utilized and is bound to glass beads. The serum sample is first treated with dithiothreitol (DTT) to reductively liberate any hcy tied up as disulfides. Excess DTT is sequestered by treatment with sodium arsenite. The pretreated sample is then combined with protected alkylating reagent (which has been labeled with $^3$H) and then combined with the glass bead-bound antibody and activating reagent. The medium is incubated for 10 minutes and the beads separated and washed. The radioactivity of the beads is then measured. The signal produced is directly related to the amount of hcy in the sample.

In an exemplary assay for hcy using protected alkylating reagent, a monoclonal antibody that specifically binds to modified hcy (and not to modified cys) is bound to a support. An analog of modified hcy, conjugated to horseradish peroxidase (HRP), is also utilized. A sample suspected of containing hcy and cys is combined with TCEP. Tris (carboxyethyl)phosphine and protected alkylating reagent in a suitable medium. TCEP, is used to reduce any homocysteine in a serum sample that is in the form of a disulfide. After enough time has elapsed for the reduction of any disulfides to occur, the anti-modified hcy-support conjugate, an activating reagent, and the modified hcy-HRP conjugate are then added to the medium. After incubation of the suspension for 30 minutes, the liquid and solid phases are separated, and the solid phase washed. An aqueous medium, to which substrate has been added is then added to the solid phase and the signal produced is inversely related to the amount of hcy in the sample.

A useful protected alkylating reagent is CABA-phosphate, which is an enol phosphate of 4-($\alpha$-chloroacetyl)-benzoic acid. This compound is found to be stable even in the presence of TCEP, unlike unprotected alkylating reagents. Because of the use of the enol phosphate protecting group, these otherwise incompatible reagents could be stored together and the assay could therefore be carried out using only two reagents. The first reagent contained TCEP, the enol phosphate of CABA, and photosensitzer dyed paticles coated with the product formed by alkylating homocysteine with CABA (hcy-ABA). Mixing of this combined reagent with the sample causes reduction of the homocysteine disulfides. The second reagent contained alkaline phosphatase and chemilumineacer beads coated with antibodies to hcy-ABA. (In general, chemiluminescer beads are latex particles into which has been incorporated a singlet oxygen activatable chemiluminescent label. Sensitizer beads are particles or beads into which a sensitizer dye has been incorporated.) Upon adding this second reagent the enol phosphate is first hydrolyzed. The resulting free CABA then reacts with homocysteine, and the hcy-ABA that is formed binds to the chemiluminescer beads. Any chemiluminescer beads still having free antibody bind to the sensitizer beads. The resulting bead pairs are detected by irradiating and measuring the ensuing chemiluminescent light emission.

CABA enol phosphates and BABA enol phosphates are described as being particularly useful, but it should be understood that they are described as being exemplary and not as limiting the invention. Other $\alpha$-haloketone enol phosphates can be similarly prepared and used as disclosed herein, as may various halovinylglycosides.

C. Singlet Oxygen Activatable Chemiluminescent Labels and Methods

Singlet oxygen activatable chemiluminescent labels and methods of making and using same are particularly useful in the methods and compositions of the present invention. It should be appreciated, however, that such labels, methods, and related compositions (e.g., labeled particles) are not the sole means of carrying out the present invention.

Thus, in various aspects of the invention, the labels, particles and other compositions described in U.S. Pat. Nos. 5,709,994, 5,340,716 and 5,478,729—the disclosures of which are incorporated by reference herein—are particularly useful as disclosed in the present specification. For example, the present invention describes the use of beads (or other matrices) labeled with chemiluminescent and/or sensitizing particles, compounds, compositions or molecules. Methods of preparing such chemiluminescent particles are described in the aforementioned U.S. patents—for example, see columns 25–33 and 41–43 of U.S. Pat. No. 5,709,994 or columns 21–22 of U.S. Pat. No. 5,340,716.

Useful photosensitizers and chemiluminescent materials are also detailed in the aforementioned patent disclosures, as are methods of attaching those materials to a matrix, whether the matrix is solid (e.g., particulate) or of a more "fluid" or "fluid/solid" nature (e.g., an oil droplet or liposome). An excellent discussion of suitable signal-producing systems can also be found in U.S. Pat. No. 5,185,243 of Ullman, et al., the disclosures of which are incorporated by reference herein.

D. Methods of Preparing Useful Antibodies

The method of this invention further involves the preparation of polyclonal and monoclonal antibodies to immunogens homologous to the immunologically distinct analyte, i.e., the "modified" analyte. The immunogen used to obtain the antibodies useful in the methods of the present invention is the modified analyte, which is obtained by reacting the compound being assayed with the selected modifying reagent. Typically, for preparation of the immunogen, first the solubilizing groups of the modifying reagents are used for attaching the reagent to an immunogenic carrier protein. Usually these attaching groups are first activated and the reagent is then coupled to the carrier protein. The resulting reagent-protein conjugate is then allowed to react with the analyte, purified, and used as an immunogen.

This invention encompasses reagents, kits and methods useful in detecting a first compound in the presence of a second compound, including instances in which the second compound is a homolog of the first. Therefore, the antibodies described above are screened for their ability to react specifically with the reaction product of the modifying reagent and either the first compound (analyte) or the second compound; i.e., for their ability to bind to either the modified analyte or to the modified second compound. For example, in an assay for hcy, the immunogen would be the derivatized hcy linked to an immunogenic carrier protein. The resulting antibodies would then be capable of specifically recognizing the modified hcy analyte and would not recognize the modified cys.

Various moieties capable of attaching the modifying reagent to the protein carrier can be used, including, for example, aldehydes, ketones, diazonium salts, alkylating agents, etc. Conveniently, carboxylic acids or sulfonic acids are converted to active esters or acid halides for conjugation. The carrier protein may be any protein, preferably one that is foreign to the animal being immunized such as keyhole limpet hemocyanin or bovine serum albumin, if the animal is, for example, a mouse, rabbit, sheep or goat.

Preparation of antibodies useful in the methods of this invention is accomplished using methods such as are well known in the art. For example, monoclonal antibodies are essentially obtained by a process similar to that described in Kohler and Milstein, *Nature* 256: 495–497 (1975). The details of the Milstein and Kohler process are well established; in general, the process involves injecting a host, usually a mouse or other suitable animal, with an immunogen. Cells are then taken from the spleen of the host animal. Alternatively, the host may comprise unsensitized spleen cells, which are sensitized to the immunogen in vitro. The resulting cells are then fused with myeloma cells; the result is a hybrid cell, referred to as a "hybridoma" that can be cultured in vitro. The population of hybridomas is screened and manipulated so as to isolate individual clones, each of which secretes a single antibody to the antigen.

When an immunogen is introduced into a host, the host's immune system responds by producing a variety of antibodies that are able to recognize various sites on the immunogen. These numerous antibodies have different affinities and specificities. To obtain those antibodies that have desirable affinity and specificity traits for the particular assay method being used, the different hybridoma cell lines are screened until an antibody having the desired characteristics is identified.

E. Preparation of Conjugates

Other applications of the foregoing method include the preparation of conjugates. For example, a protein that has sulfhydryl groups may be labeled with no more than one molecule of CABA enol phosphate per protein molecule. The conjugate is stable because CABA phosphate is not an alkylating agent. This labeled material is then admixed with an excess of a sulfhydryl-containing protein. Addition of alkaline phosphatase initiates a coupling reaction which would be nearly quantitative because of the high reactivity of CABA.

Thus, reasonable yields of 1:1 protein conjugates are readily achieved without interfering polymerization of the CABA-labeled protein. Similarly, drug conjugates are prepared via similar methods as those described above; e.g., a sulfhydryl-containing drug is used instead of a sulfhydryl-containing protein.

F. Kits

As a matter of convenience, the reagents for use in the present invention can be provided in a kit for use in an assay method, in a method of conjugating one molecule to another (e.g., protein conjugation), or in any practical application of the invention. A typical kit for use in a method for detecting hcy comprises in a packaged combination: a protected alkylating reagent capable, upon activation, of chemically modifying hcy and cys to form modified hcy and modified cys, an antibody capable of specifically binding to the modified hcy but not to the modified cys, and an activating reagent. The kit can further comprise a labeled analog of the modified hcy.

As noted elsewhere herein, modified hcy may comprise the product formed by the interaction of an alkylating reagent with homocysteine in the sample—e.g., modification of the sulfhydryl groups may occur. In one variation, the modified homocysteine is a carboxyphenacyl thioether of homocysteine (hcy-ABA).

The kit can also comprise a releasing agent. Suitable releasing agents capable of liberating the hcy and cys sulfur compounds from serum proteins are well known in the art and include, without limitation, reducing agents such as sodium and potassium borohydride; thiols such as dithiothreitol, dithioerythritol, 2-mercaptoethanol, thioglycolic acid and glutathione; and phosphines and trialkylphosphines such as tributylphosphine and tris(2-carboxyethyl) phosphine. Particularly suitable reducing agents are dithiothreitol and tris(2-carboxyethyl)phosphine (TCEP), the latter of which is described in Burns, et al., J. Org. Chem. 56(8):2648–2650 (1991), agent suitable for releasing any Hcy in the disulfide form.

A kit for coupling of two molecules in an aqueous medium will preferably include a protected alkylating reagent having an attaching group and an activating reagent in separate containers.

Under appropriate circumstances, one or more of the reagents in the kit can be provided in solution or as a dry powder, usually lyophilized, including excipients, which on dissolution will provide for a reagent solution having the appropriate concentrations for performing a method or assay in accordance with the present invention. To enhance the versatility of the subject invention, the reagents can be provided in packaged combination, in the same or separate containers, so that the ratio of the reagents provides for substantial optimization of the method and assay. The reagents may each be in separate containers or various reagents can be combined in one or more containers, depending on the cross-reactivity and stability of the reagents. As a matter of convenience, the reagents employed in the present invention can readily be provided in predetermined amounts. The kit can also contain written instructions on how to use the reagents and/or how to perform a particular assay, for example in the form of a package insert.

It should also be understood that various combinations of the embodiments described herein are included within the scope of the present invention. Other features and advantages of the present invention will be apparent from the descriptions hereinabove, from the Examples to follow, and from the claims.

ABBREVIATIONS

Tris HCl—Tris(hydroxymethyl)aminomethane-HCl (a 10× solution) from BioWhittaker, Walkersville, Md.

DTT—dithiothreitol from Sigma Chemical Company, St. Louis, Mo.

HPLC—high performance liquid chromatography.

DPP—4,7-diphenylphenanthroline from Aldrich Chemical Company, Milwaukee Wis.

BSA—bovine serum albumin from Sigma Chemical Company, St. Louis Mo.

ELISA—enzyme linked immunosorbent assay as described in "Enzyme-Immunoassay," Edward T. Maggio, CRC Press, Inc., Boca Raton, Fla. (1980)

g—grams mmol—millimolar

DMF—dimethyl formamide

THF—tetrahydrofuran

MS—mass spectroscopy

NMR—nuclear magnetic resonance spectroscopy

TMSCl—trimethylsilylchloride

EDAC—1-ethyl-3-(3-dimethylaminopropyl)-carbodiimide hydrochloride.

MES—2-(N-morpholino)ethane sulfonic acid.

SPDP—N-succinimidyl 3-(2-pyridylthio)-propionate.

Sulfo-SMCC—4-(N-maleimidomethyl)cyclohexane-1-carboxylate.

TCEP—tris-carboxyethyl phosphine.

EXAMPLES

The following examples illustrate, but do not limit, the present invention.

Example 1

Demonstration of Deprotection of the Alkylating Group

1. Deprotection of a Phosphate Protecting Group by Alkaline Phosphatase

A mixture of BABA-phosphate and CABA-phosphate (resulting from preparation of BABA-phosphate), 5 mg in 1 mL pH 8–9 NaOD/$D_2O$ is treated with 1 mg (15 units) of alkaline phosphatase (Sigma, human placenta) for 15 minutes at room temperature. TLC analysis (250 micron $SiO_2$ (Analtech Uniplate), using 20% $H_2O$/ACN indicates that the phosphate group of the protected alkylating reagent is removed by treatment with alkaline phosphatase, whereas the nontreated protected alkylating reagent remains intact. This is further corroborated by NMR ($D_2O$) analysis, which shows the disappearance of the vinyl proton peak (normally found at 6.3 ppm for the enol-phosphate).

Further demonstration of the efficient removal of the protecting group is shown by TLC (as above) analysis of the reaction of the deprotected alkylating reagent with cysteine.

Reaction of the crude product of the reaction with alkaline phosphatase, for about ten (10) minutes, with cysteine, results in the disappearance of the first product, deprotected alkylating reagent, and appearance of a more polar product. The latter is assumed to be an adduct of the alkylating reagent and cysteine.

2. Stability of a Protected Alkylating Reagent in the Presence of a Reducing Agent The stability of a mixture of CABA-phosphate (protected alkylating reagent) and a reducing agent (tris(carboxyethyl) phosphine or TCEP) is demonstrated by TLC analysis, as described above, using BABA, CABA-phosphate and TCEP as standards. Analysis of a mixture of BABA and TCEP (5 mM each in phosphate buffer pH 7) demonstrates that the reaction of the alkylating agent with the reducing agent is nearly complete following incubation of the mixture for 30 minutes at room temperature. Unlike the free alkylating reagent, the protected alkylating reagent (CABA phosphate) is found to be resistant to reaction with TCEP following incubation of a mixture of the two reagents (5 mM each in phosphate buffer, pH 7) for sixteen (16) hours at room temperature.

Example 2

Homocysteine Assay Using LOCI

Luminescent Oxygen Channeling Immunoassay

A variety of assay methods and compositions are useful in the detection of compounds and compositions in biological samples—e.g., serum samples. One useful assay which uses the compositions and methods described herein is referred to herein as LOCI. (See U.S. Pat. Nos. 5,709,994, 5,340,716 and 5,478,729—the disclosures of which are incorporated by reference herein—for further details regarding luminescent oxygen channeling immunoassays.)

Hcy exists in numerous forms in plasma—e.g., as a small percentage in the free form, some as disulfides with itself and cysteine, and some as disulfides with albumin (about 70%). Total hcy is the clinically-relevant measure, however, with reference values in fasting subjects of about 5 to 15 $\mu$mol/L. Even a moderate increase in plasma hcy, referred to as hyperhomocysteinemia, is considered a risk factor for premature cardiovascular diseases in the general population.

Antibody-based assays are popular formats and would be readily adaptable into an automated form with high throughputs if the problem of sample pretreatment—particularly off-line sample pretreatment—could be resolved. Thus, the present disclosure of a means allowing the rapid and fully automated detection of homocysteine (hcy) and/or other molecules and compositions is a valuable tool that is readily demonstrated using the within-disclosed methods and compositions.

In essence, the steps of such an assay include (1) conversion of hcy disulfides into free hcy, e.g., with tris-(2-carboxyethyl)phosphine hydrochloride reduction; (2) derivatization of hcy with bromoacetylbenzoic acid (BABA) or an enol phosphate derivative of BABA to produce hcy-ABA; and (3) detection and quantitation of hcy-ABA by LOCI. The assay is further enhanced via the use of protected haloketones, e.g., enol phosphate derivatives of BABA or CABA, as these derivatizing agents have better solubility over a wide pH range and a longer shelf-life than unprotected forms. In addition, the use of such protected haloketones has the additional advantage of simplicity, in that it allows the use of a two-reagent protocol, even in an automated context.

For purposes of illustration, an automated assay method is described herein. It should be understood that non-automated assays and assays utilizing different components and steps are also contemplated for use with the compositions of the present invention and are thus within its scope.

A. Materials

The following reagents, which are used in various methods described below, may be purchased from the commercial sources indicated but are readily available from a wide variety of other sources. Bovine serum albumin (BSA; ICN Pharmaceuticals, Costa Mesa, Calif.); calf intestinal alkaline phosphatase (CIAP; Pierce Chemicals, Rockford, Ill.); sulfosuccinimidyl 6-(biotinamido) hexanoate (NHS-LC-Biotin; Pierce, Rockford, Ill.); L-homocystine, cysteine and methionine (Sigma, St. Louis, Mo.); L-homocysteine thiolactone hydrochloride (HCTL; Fluka, Milwaukee, Wis.); tris-(2-carboxyethyl)phosphine, hydrochloride (TCEP; Molecular Probes, Eugene, Oreg.); Dextran T-500 (Pharmacia Co., Piscataway, N.J.); HBR-1 (Heterophilic Blocking Reagent 1; Scantibodies Lab., Inc., Santee, Calif.). Unless specified otherwise, it should be presumed that all other chemicals used herein are reagent grade.

The following reagents were prepared in-house: bromoacetylbenzoic acid (BABA); bromoacetylbenzoic acid N-hydroxysuccinamide ester (BABA-NHS); "pro-CABA" or CABA-phosphate (an enol phosphate derivative of CABA); and homocysteine-acetylbenzoic acid (hcy-ABA). An anti-hcy-ABA monoclonal antibody (e.g., clone I5C12 to hcy-ABA-BSA conjugate from Syva's monoclonal group) is used as described below. Other equivalent, useful monoclonal and polyclonal antibodies may readily be generated independently via techniques known to those of skill in the art (see, e.g., Section D above).

Serum calibrators are prepared with known amounts of homocysteine spiked into serum samples of pooled normal individual sera. The homocysteine level in this pooled serum is determined by HPLC according to standard techniques. For example, many reference labs—e.g., the Cleveland Clinic, Cleveland, Ohio—are equipped to perform such protocols.

A solid matrix, preferably one in bead form, is labeled with anti-hcy-ABA monoclonal antibodies (mAbs); what we refer to herein as "Ab-acceptor beads" are prepared essentially as follows. Polystyrene beads are dyed first with acceptor dye (e.g. C-28 thioxene, DPP/Eu(TTA)3) then coated with dextran.

C-28 thioxene was prepared as follows:

To a solution of 4-bromoaniline (30 g, 174 mmol) in dry DMF, (200 mL) was added 1-bromotetradecane (89.3 mL, 366 mmol) and N,N-diisopropylethylamine (62.2 mL, 357 mmol). The reaction solution was heated at 90° C. for 16 hr under argon before being cooled to room temperature. To this reaction solution was again added 1-bromotetradecane (45 mL, 184 mmol) and N,N-diisopropylethylamine (31 mL, 178 mmol) and the reaction mixture was heated at 90° C. for another 15 hr. After cooling, the reaction solution was concentrated in vacuo and the residue was diluted with $CH_2Cl_2$ (400 mL). The $CH_2Cl_2$ solution was washed with 1N aqueous NaOH (2×), $H_2O$, and brine, was dried over $Na_2SO_4$ and was concentrated in vacuo to yield a dark brown oil (about 110 g). Preparative column chromatography on silica gel by a Waters 500 Prep LC system eluting with hexane afforded a yellow oil that contained mainly the product (4-bromo-N,N-di-($C_{14}H_{29}$)-aniline) along with a minor component 1-bromotetradecane. The latter compound was removed from the mixture by vacuum distillation (bp 105–110° C., 0.6 mm) to leave 50.2 g (51%) of the product as a brown oil. To a mixture of magnesium turnings (9.60 g, 395 mmol) in dry THF (30 mL) under argon was added dropwise a solution of the above substituted aniline product (44.7 g, 79 mmol) in THF (250 mL). A few crystals of iodine were added to initiate the formation of the Grignard reagent. When the reaction mixture became warm and began to reflux, the addition rate was regulated to maintain a gentle reflux. After addition was complete, the mixture was heated at reflux for an additional hour. The cooled supernatant solution was transferred via cannula to an addition funnel and added dropwise (over 2.5 hr) to a solution of phenylglyoxal (11.7 g, 87 mmol) in THF (300 mL) at −30° C. under argon. The reaction mixture was gradually warmed to 0° C. over 1 hr and stirred for another 30 minutes. The resulting mixture was poured into a mixture of ice water (800 mL) and ethyl acetate (250 mL). The organic phase was separated and the aqueous phase was extracted with ethyl acetate (3x). The combined organic phases were washed with $H_2O$ (2x), brine and were dried over $MgSO_4$. Evaporation of the solvent gave 48.8 g of the crude product as a dark green oily liquid. Flash column chromatography of this liquid (gradient elution with hexane, 1.5:98.5, 3:97, 5:95 ethyl acetate:hexane) afforded 24.7 g (50%) of the benzoin product (MS ($C_{42}H_{69}NO_2$): [M−H]+618.6, 1NMR (250 MHz, $CDEL_3$) was consistent with the expected benzoin product. To a solution of the benzoin product from above (24.7 g, 40 mmol) in dry toluene (500 mL) was added sequentially 2-mercaptoethanol (25 g, 320 mmol) and TMSCl (100 mL, 788 mmol). The reaction solution was heated at reflux for 23 hr under argon before being cooled to room temperature. To this was added additional TMSCl (50 mL, 394 mmol); and the reaction solution was heated at reflux for another 3 hr. The resulting solution was cooled, was made basic with cold 2.5N aqueous NaOH and was extracted with $CH_2Cl_2$ (3x). The combined organic layers were washed with saturated aqueous $NaHCO_3$ (2x) brine, dried over $Na_2SO_4$ and was concentrated in vacuo to give a brown oily liquid. Preparative column chromatography on silica gel by using a Waters 500 Prep LC system (gradient elution with hexane, 1:99, 2:98 ethyl acetate:hexane) provided 15.5 g (60%) of the C-28 thioxene as an orange-yellow oil (MS ($C_{44}H_{71}NOS$): [M−H]+661.6, 1H NMR (250 MHz, $CDC_{13}$) was consistent with the expected C-28 thioxene product 2-(4-(N,N-di-($C_{14}H_{29}$)-anilino)-3-phenyl thioxene.

DPP/Eu(TTA)3 was prepared as follows:

8.69 g of Eu(TTA)3 . $3H_2O$ (10 mmoles, Kodak Chemical Company, Rochester N.Y.) and 1.8 g of 1,10-phenanthroline (10 mmoles, Aldrich) were combined in 50 mL of dry toluene and heating to 95° C. in an oil bath for 1 hour. Toluene was removed under reduced pressure. The ash colored solid was crystallized from 10 mL of toluene to yield 10 grams of DPP/Eu(TTA)3. Absorption spectrum: 270 nm (20,000), 340 nm (60,000) (Toluene) 1.R(KBr): $Cm^{-1}$: 3440(s), 1600(s), 1540(s), 1400(s), 1300(s).

Carboxyl acceptor beads were prepared as follows:

The starting beads were carboxylate-modified latex purchased from Seradyn Particle Technology, Indianapolis, Ind. Four mL of 10% suspension (400 mg) of washed 175 nm carboxylate modified latex was diluted with 3 mL of ethoxyethanol in a 25 mL round bottom (R.B.) flask with a stir bar. The R.B. flask was then placed in an oil bath at 105° C. and stirred for 10 minutes. Then, 3.3 mM C-28 thioxene and 15.5 mM Eu(TTA)3DPP in benzyl alcohol was added; the beads were stirred for 5 minutes more.

At this point, 1.0 mL of 0.1N NaOH was added slowly over 5 minutes. During all the additions, the oil bath temperature was maintained at 105° C. The oil bath temperature was slowly allowed to drop to room temperature over 2 hours. After cooling, the mixture was diluted with 20 mL of ethanol and centrifuged (12,500 rpm, 30 minutes). Supernatants were discarded and the pellets resuspended in ethanol by sonication. Centrifugation was repeated, and the pellet was resuspended in water; and centrifugation was repeated. The pellet was resuspended in 5 mL of aqueous ethanol to a final volume of 40 mL.

Preparation of aminodextran:

Hydroxypropylaminodextran:

($1NH_2$/7 glucose) was prepared by dissolving Dextran T-500 (Pharmacia, Uppsala, Sweden) (50 g) in 150 mL of $H_2O$ in a 3-neck round-bottom flask equipped with mechanical stirrer and dropping funnel. To the above solution was added 18.8 g of Zn $(BF_4)_2$ and the temperature was brought to 87° C. with a hot water bath. Epichlorohydrin (350 mL) was added dropwise with stirring over about 30 min while the temperature was maintained at 87–88° C. The mixture was stirred for 4 hr while the temperature was maintained between 80° C. and 95° C., then the mixture was cooled to room temperature. Chlorodextran product was precipitated by pouring slowly into 3 L of methanol with vigorous stirring, recovered by filtration and dried overnight in a vacuum oven.

The chlorodextran product was dissolved in 200 mL of water and added to 2 L of concentrated aqueous ammonia (36%). This solution was stirred for 4 days at room temperature, then concentrated to about 190 mL on a rotary evaporator. The concentrate was divided into two equal batches, and each batch was precipitated by pouring slowly into 2 L of rapidly stirring methanol. The final product was recovered by filtration and dried under vacuum.

Hydroxypropylaminodextran ($1NH_2$/7 glucose), prepared above, was dissolved in 50 mM MOPS, pH 7.2, at 12.5 mg/mL. The solution was stirred for 8 hr at room temperature, stored under refrigeration and centrifuged for 45 min at 15,000 rpm in a Sorvall RC-5B centrifuge immediately before use to remove a trace of solid material. To 10 mL of this solution was added 23.1 mg of Sulfo-SMCC in 1 mL of water. This mixture was incubated for 1 hr at room temperature and used without further purification.

Maleimide aminodexran (MAD) was prepared as follows:

Sulfo-SMCC (11.55 mg) was dissolved in 0.5 mL distilled water. Slowly, during 10 sec, the above solution was added to 5 mL of stirring aminodextran, prepared above, solution (12.5 mg/mL in 50 mM MOPS, pH 7.2). The mixture was incubated for 1 hr at room temperature.

To the stirring solution above was added 5 mL of 20 mg/mL (100 mg) of the sensitizer beads prepared on page 46 in distilled water. (Then, 1 mL of 200 mg/mL NHS (prepared fresh in 50 mM MES, pH adjusted to 6.0 with 6N NaOH) was added. 200 mg EDAC was dissolved in 1 mL distilled water and this solution was added slowly with stirring to the sensitizer beads. The pH was adjusted to 6.0 by addition of 450 μL of 1N HCl and the mixture was incubated overnight in the dark. A solution of 100 mg of succinic anhydride in 0.5 mL of DMSO was added to the sensitizer beads and the mixture was incubated for 30 min at room temperature in the dark. To this mixture was added 0.13 mL 10% Tween-20 bringing the final concentration of Tween-20 to 0.1%. The beads were centrifuged for 45 min at 15,000 rpm as above. The supernatant was discarded and the beads were resuspended in 10 mL of buffer (50 mM MOPS, 50 mM EDTA and 0.1% Tween-20, pH 7.2). The mixture was sonicated to disperse the beads. The beads were centrifuged for 30 min as described above, the supernatant was discarded and the beads were resuspended. This procedure was repeated for a total of three times. Then, the beads were resuspended to 40 mg/mL in 2.5 mL of the above buffer, saturated with argon and Tween-20 was added to a concentration of 0.1%. The beads were stored at 4° C.

Acceptor Beads coated with MAD were prepared as follows:

Carboxyl acceptor beads prepared above (99 mg in 4.5 mL water) were added slowly with vortexing to 5.5 mL of MAD (maleimide aminodextran) from above, followed by 1 mL of 200 mg/mL NHS in 50 mM MES, pH 6, 1 mL of 200 mg/mL EDAC in water, and 450 µL of 1 M HCl, final pH 6. The mixture was incubated overnight at room temperature in the dark, then reacted with 200 mg succinic anhydride in 0.5 mL of DMSO for 30 min at room temperature. Freshly opened Surfact-Amps Tween-20 (Pierce Chemical Company, Rockford, Ill.) was added and the beads were centrifuged 30 min at 15,000 rpm in a Sorvall RC-5B centrifuge, washed by centrifugation with three 10 mL portions of 50 mM MOPS, 50 mM EDTA, 0.1% Surfact-Amps Tween-20 (Pierce Chemical Company), pH 7.2, and resuspended in 3 mL of the same.

Antibody coated acceptor beads were prepared as follows:

Monoclonal anti-hcy-ABA Ab was thiolated by mixing 622 µL (4.28 mg) with 10.2 µL of SATA (1.25 mg/mL in ethanol, 2 eq.), incubating for 1 hr at room temperature and dialyzing cold against 2×2 L of 150 mM NaCl, 10 mM $Na_2HPO_4$, 1 mM EDTA, pH7. The thioacetylated antibody was deacetylated by adding 62.2 µL of hydroxylamine (1 M $H_2NOH$, 50 mM MOPS, 25 mM EDTA, pH 7), bubbling with argon and incubating for 1 hr at room temperature. The product was applied to a Pharmacia PD-10 column (G-25) and eluted with 50 mM MOPS, 50 mM EDTA, pH 7.2, bubbled with argon. After 2.5 mL fore-run, three-1 mL fractions were collected and combined. Recovery of antibody was 3.66 mg or 86% by A280. Surfact-Amps Tween-20 (10%) was added to give 0.2% final concentration.

A 1.4 mL aliquot of the thiolated antibody above (1.71 mg antibody) was immediately added to 300 µL (10 mg) of maleimidated beads prepared above plus enough 10% Tween-20 to bring final concentration in the mixture to 0.2%. The tube was purged with argon and incubated overnight at room temperature in the dark. To the above was added 3.4 µL of 1 M $HSCH_2COOH$ in water. After 30 min at room temperature, 6.8 µL of $ICH_2COOH$ (1 M in water) was added. After 30 min 3.5 mL of 0.17M glycine, 0.1M NaCl, 0.1% (v/v) Tween-20, 10 mg/mL BSA, pH 9.2 was added and the beads were centrifuged (30 min at 15,000 rpm), incubated for 3 hr in 5 mL of the same buffer, centrifuged, washed by centrifugation with three-5 mL portions of Buffer C, resuspended in 5 mL of Buffer C and stored under refrigeration. The size of the beads, determined in Buffer C, was 301±56 nm.

Beads that may be termed "sensitizer" beads herein are labeled with hcy-ABA (hcy-sensitizer beads). Preparation of polystyrene beads dyed with sensitizer dye (e.g. silicon tetra-t-butyl phthalocyanine) is carried out essentially as follows.

Silicon tetra-t-butyl phthalocyanine:

Sodium metal, freshly cut (5.0 g, 208 mmol), was added to 300 mL of anhydrous methanol in a two-liter, 3-necked flask equipped with a magnetic stirrer, reflux condenser, a drying tube and a gas bubbler. After the sodium was completely dissolved, 4-t-butyl-1,2-dicyanobenzene (38.64 g, 210 mmol, from TCI Chemicals, Portland Oreg.) was added using a funnel. The mixture became clear and the temperature increased to about 50° C. At this point a continuous stream of anhydrous ammonia gas was introduced through the glass bubbler into the reaction mixture for 1 hr. The reaction mixture was then heated under reflux for 4 hr. while the stream of ammonia gas continued. During the course of the reaction, a solid started to precipitate. The resulting suspension was evaporated to dryness (house vacuum) and the residue was suspended in water (400 mL) and filtered. The solid was dried (60° C., house vacuum, $P_2O_5$). The yield of the product (1,3-diiminoisoindoline, 42.2 g) was almost quantitative. This material was used for the next step without further purification. To a one-liter, three-necked flask equipped with a condenser and a drying tube was added the above product (18 g, 89 mmol) and quinoline (200 mL, Aldrich Chemical Company, St. Louis Mo.). Silicon tetrachloride (11 mL, 95 mmol, Aldrich Chemical Company) was added with a syringe to the stirred solution over a period of 10 minutes. After the addition was completed, the reaction mixture was heated to 180–185° C. in an oil bath for 1 hr. The reaction was allowed to cool to room temperature and concentrated HCl was carefully added to acidify the reaction mixture (pH 5–6). The dark brown reaction mixture was cooled and filtered. The solid was washed with 100 mL of water and dried (house vacuum, 60° C., $P_2O_5$). The solid material was placed in a 1-liter, round bottom flask and concentrated sulfuric acid (500 mL) was added with stirring. The mixture was stirred for 4 hr. at 60° C. and was then carefully diluted with crushed ice (2000 g). The resulting mixture was filtered and the solid was washed with 100 mL of water and dried. The dark blue solid was transferred to a 1-liter, round bottom flask, concentrated ammonia (500 mL) was added, and the mixture was heated and stirred under reflux for 2 hr., was cooled to room temperature and was filtered. The solid was washed with 50 mL of water and dried under vacuum (house vacuum, 60° C., $P_2O_5$) to give 12 g of product silicon tetra-t-butyl phthalocyanine as a dark blue solid. 3-picoline (12 g, from Aldrich Chemical Company), tri-n-butyl amine (anhydrous, 40 mL) and tri-n-hexyl chlorosilane (11.5 g) were added to 12 g of the above product in a one-liter, three-necked flask, equipped with a magnetic stirrer and a reflux condenser. The mixture was heated under reflux for 1.5 hr. and then cooled to room temperature. The picoline was distilled off under high vacuum (oil pump at about 1 mm Hg) to dryness. The residue was dissolved in $CH_2Cl_2$ and purified using a silica gel column (hexane) to give 10 g of pure product di-(tri-n-hexylsilyl)-silicon tetra-t-butyl phthalocyanine as a dark blue solid. (LSIMS: $[M-H]^+$ 1364.2, absorption spectra: methanol: 674 nm ($\epsilon$180,000): toluene 678 nm, $^1$H NMR (250 MHz, $CDCl_3$): δ: −2.4(m,12H), −1.3(m, 12H), 0.2–0.9 (m, 54H), 1.8(s, 36H), 8.3(d, 4H) and 9.6 (m, 8H) was consistent with the above expected product.

Preparation of sensitizer dyed beads:

The sensitizer beads were prepared by placing 600 mL of 10% solid carboxylate modified beads (Seradyn) in a three-necked, round-bottom flask equipped with a mechanical stirrer, a glass stopper with a thermometer attached to it in one neck, and a funnel in the opposite neck. The flask had been immersed in an oil bath maintained at 94±1° C. The beads were added to the flask through the funnel in the neck and the bead container was rinsed with 830 mL of ethoxyethanol, 1700 mL of ethylene glycol and 60 mL of 0.1N NaOH and the rinse was added to the flask through the funnel. The funnel was replaced with a 24–40 rubber septum. The beads were stirred at 765 rpm at a temperature of 94±1° C. for 40 min.

Silicon tetra-t-butyl phthalocyanine (10.0 g) was dissolved in 300 mL of benzyl alcohol at 60±5° C. was added to the above round bottom flask through the septum by means of a syringe heated to 120±10° C. at a rate of 3 mL per min. After 15 min 900 mL of deionized water and 75 mL of 0.1N NaOH was added. dropwise over 40 min. The temperature of the oil bath was allowed to drop slowly to 40±10° C. and stirring was then discontinued. The beads were then filtered through a 43 micron polyester filter and subjected to a Microgon tangential flow filtration apparatus (Microgon Inc., Laguna Hills, Calif.) using ethanol:water, 100:0 to 10:90.

Preparation of hcy-ABA sensitizer beads:

Immobilization of hcy-ABA onto particles—e.g. onto sensitizer beads—is carried out essentially as follows (see also U.S. Pat. No. 5,478,729, the disclosures of which are incorporated by reference herein). First, carboxy-sensitizer beads are converted to aminodextran-coated sensitizer beads according to the following protocol. 135 mg aminodextran was disolved in 1.35 ml of 0.2M MES pH 6.0 with stirring; then 9.0 ml carboxy-sensitizer beads at 3 mg/ml are spun down and resuspend into 1.35 ml deionized $H_2O$ each. Beads were added dropwise to aminodextran solution with stirring followed by 177.2 $\mu$l EDAC at 80 mg/ml deionized $H_2O$; and the mixture was incubated at room temperature (r.t.) overnight in the dark. Next, 5N NaCl was added to produce a final concentration of 0.5N and the mixture was incubate for 30 minutes at r.t. Finally, the bead suspension was spun down and washed with 4×5 ml 0.1M phosphate buffer containing 0.1N MaCl and 10 mM EDTA pH 7.0, and stored in the same buffer at 24 mg beads/ml.

Next, the following reaction with BABA-NHS was carried out. (1) 1.0 ml of the aminodextran-coated beads (24 mg/ml), were spun down and resuesended in 0.5 ml in 0.1M phosphate with 0.1N NaCl pH 7.0. (2) 28 mg BABA-NHS were dissolved in 1.0 ml DMSO and 250 $\mu$l was added to each aminodextran-coated bead suspension followed by 250 $\mu$l 0.1M phosphate buffer pH 7.0. The reaction mixture was incubated for 1.5 hr at room temperature. (3) 0.5 ml of 0.1M phosphate, pH 7.0 was added and the reaction mixture was further incubated for 1 hr. (4) The beads were span down and washed with 4×6 ml 0.1M phosphate (pH 7.0), and resuspended in 1.0 ml of the same buffer.

The above beads were then reacted with homocysteine thiolactone hydrochloride (HCTL), as follows: 92.5 mg HCTL was dissolved in 1.25 ml 1.0N NaOH and incubated for 10 minutes at 37° C. 5 ml of 0.5M phosphate buffer pH 7.0 was added (bring the pH to 7.0). The reaction mixture was purged with nitrogen gas. 1.0 ml of the HCTL solution was added in two aliquots to 1.0 ml degassed bead suspension from step (4) in the preceding paragraph. The reaction mixture was incubated at 37° C. for 4 hrs, and the beads were blocked with 5 ml of 0.17M glycine, 0.1M NaCl, 10 mg/ml BSA, 10 mM EDTA pH 9.2 buffer for 1 hr. at r.t. The bead suspension was washed with 1×5 ml buffer of 0.17M glycine, 0.1M NaCl, 10 mg/ml BSA, 10 mM EDTA pH 9.2, followed by 4×5 ml LOCI of buffer, and stored at 4° C. in 5.0 ml. of LOCI buffer.

The general assay buffer used herein, which is also identified as "LOCI buffer," includes the following: 0.1M Tris base, 0.3M NaCl, 25 mM EDTA, 0.1% BSA, 0.1% Dextran T-500, 0.05% Kathon, 0.01% Gentamicin, 0.1% Zwittergent 3–14 and HBR-1@1/320. Adjust pH to 8.2 with concentrated HCl (milli-Q water is used in this buffer preparation).

Related buffers are prepared as follows: LOCI Prestress Buffer: LOCI buffer contains 10 mM bis-Tris and adjust pH to 9.0. LOCI hcy Assay Buffer (Assay Buffer): 50 mM Borate buffer, 0.3M NaCl, 0.1% Dextran T-500, 0.05% Kathon, 0.01% Gentamicin, 0.1% Tween-20 and HBR-1 at 1/50 dilution of the stock solution. Adjust pH to 9.2.

The reaction admixture is incubated at 37° C. for 4 hrs. and the beads are blocked with 5 ml of 0.17M glycine, 0.1M NaCl, 10 mg/ml BSA, 10 mM EDTA pH 9.2 buffer for 1 hr. at r.t. the bead suspension is washed with 1×5 ml buffer of 0.17M glycine, 0.1M NaCl, 10 mg/ml BSA, 10 mM EDTA pH 9.2, followed by 4×5 ml LOCI buffer, and stored at 4° C. in 5.0 ml LOCI buffer.

Related buffers are prepared as follows. LOCI Prestress Buffer: LOCI buffer contains 10 mM bis-Tris and adjust pH to 9.0. LOCI hcy Assay Buffer (Assay Buffer): 50 mM Borate buffer, 0.3M NaCl, 0.1% Dextran T-500, 0.05% Kathon, 0.01% Gentamicin, 0.1% Tween-20 and HBR-1 at 1/50 dilution of the stock solution. Adjust pH to 9.2.

The following assay protocols are preferably performed on an automated instrument (e.g., an automated Tecan-1 instrument) but may also be adapted for use with other automated instruments or for non-automated uses. Those of skill in the relevant art are able to modify the following protocols accordingly.

B. Three-reagent Protocol

A 50 $\mu$L mixture of hcy-ABA-sensitizer beads (0.1 mg/ml) and 2 mM TCEP is added to 5 $\mu$L hcy serum calibrator in a reaction cuvette, followed by the addition of 50 $\mu$L assay buffer. The mixture is incubated for 417 sec. Then, 50 $\mu$L of 5 mM BABA is added and followed by 45 $\mu$L assay buffer. Following incubation for 157 sec., 50 $\mu$L of Ab-coated acceptor beads (at 0.25–0.5 mg/ml) is added. After incubation for 154 sec., the sample is read.

C. Two-reagent Protocol

Due to the incompatibility of the bromoacetyl benzoic acid (BABA) with the other reagents, as well as its limited solubility and stability, an enol phosphate derivative of CABA (CABA-phosphate), a pro-CABA compound, is also studied. A further advantage of using an enol phosphate derivative of a haloketone as a derivatizing agent is the possibility of using the two-reagent protocol with an automated instrument such as that utilized in automated LOCI assays.

A 50 $\mu$L mixture of hcy-ABA-sensitizer beads (0.1 mg/ml) and 2 mM TCEP and 5 mM CABA-phosphate is added to 5 $\mu$L hcy serum calibrator in a reaction cuvette, followed by the addition of 100 $\mu$L assay buffer. The mixture is incubated for 417 sec. Then, a 50 $\mu$L mixture of Ab-coated acceptor beads (0.5 mg/ml) and alkaline phosphatase (1 mg/ml) is added, followed by 45 $\mu$L assay buffer. Following incubation for 157 sec, the sample is read as in the three-reagent standard protocol.

D. Performance of Three-reagent Protocol with BABA

In the so-called three reagent assay format, hcy-sensitizer beads mixed with TCEP are used as the first reagent. Ab-coated acceptor beads are used as the third reagent which is added following the sample derivatization step. This results in an even competition between the soluble and the bead-bound hcy-ABA for Ab on acceptor beads in the third step. Maximum signal is obtained in the absence of hcy in serum, due to the specific bead aggregation. This bead aggregation is inhibited by hcy in the serum sample so that the signal is inversely proportional to the amount of hcy in serum. Homocysteine in buffer is used as the calibrators.

A LOCI homocysteine assay is performed by the automated LOCI Tecan instrument. The reagents and serum samples are kept at 4° C. on this instrument, but the assay buffer and reaction cuvettes are kept at 37° C. The assay is performed at 37° C., and the three-reagent protocol is used, as described herein, while the two-reagent assay protocol is also used in subsequent work with CABA-phosphate as an alternate derivatizing reagent.

A homocysteine standard curve is constructed using six calibrators prepared by spiking homocysteine into pooled serum which is quantitated by HPLC. Over 60% signal modulation is obtained using 2% serum sample (data not shown). The volumes of the reaction mixture at various steps are optimized for maximum concentration of the reducing agent, since this step is slower than the alkylation step. The final amount of TCEP used is lower than the alkylating agent.

The intra-assay CV's are obtained by determination of the calibrators in replicates (using the same sample). The CV's of the signal measurement and the concentration determination are shown in Table 1. In Table 1, the three-reagent assay protocol and the two-reagent assay protocol are used as described above.

The stability of BABA is studied at three different pH conditions as shown in Table 2. In Table 2, the three-reagent protocol is used as described previously, with 5 mM BABA stored in a different pH buffer as R-2 (reagent 2).

The activity of BABA is monitored by the amount of total assay signal modulation obtained by LOCI using the three-reagent protocol. Only limited stability of BABA is obtained even at the optimum condition which is at pH 6.0.

E. Performance of CABA-Phosphate as Derivatizing Agent

An enol phosphate derivative of CABA is synthesized. CABA-phosphate is readily soluble over a wide pH range and is inactive until triggered by an enzyme, which is added at the defined step in the assay. Therefore, it has the potential for a two-component assay. In the two-reagent protocol, reagent-1 (R1) is a mixture of hcy labeled sensitizer beads at 50 μg/ml, 2 mM TCEP, and 5 mM CABA-phosphate in assay buffer; Reagent-2 (R-2) is Ab-coated acceptor beads at 0.1 mg/ml mixed with alkaline phosphatase at 1 mg/ml in assay buffer. In this protocol, 50 μl of R1, 5–10 μl of sample and 50 μl of assay buffer are mixed and incubated for 7 min at 37° C. (step 1), then 50 μl of R2 and 100 μl of assay buffer are added. The reaction mixture is incubated further for 3 minutes. The LOCI reading is performed as described above. The standard curve of hcy serum calibrators using CABA-phosphate as derivatizing agent and the two-reagent protocol is determined (not shown). Over 60% signal modulation is obtained using 2% serum sample.

The three-reagent assay protocol using CABA-phosphate as derivatizing agent is also assessed. Similar results are obtained with hcy serum calibrators as in the three-reagent protocol using BABA (not shown). The stability of CABA is also studied. The activity of CABA-phosphate as derivatizing agent is monitored by the amount of total assay signal modulation obtained by LOCI using the three-reagent protocol. It has a much longer shelf life than BABA as shown in Table 3. In Table 3, the three-reagent assay protocol is used with CABA-phosphate stored at two temperatures in pH 9.0 as R-2; mixed hcy-sensitizer beads and TCEP as R-1; mixed Ab-acceptor beads and alkaline phosphatase as R-3.

F. Correlation Studies

The same three-reagent protocol used with BABA, as well as with CABA-phosphate as derivatizing agent, is used in this correlation study. The results are shown in Table 4-a. Similar results are obtained with either BABA or CABA-phosphate as the derivatizing agent using the three-reagent protocol by LOCI as shown in Table 4-a. The correlation of LOCI vs. HPLC using the two-reagent protocol is shown in Table 4-b. The two reagent protocol yields somewhat better correlation with HPLC than the three-reagent protocol. This result may indicate better assay precision with the two-reagent protocol than the three-reagent protocol even with the automated instrument. Thus, the feasibility of a rapid—and even fully-automated—antibody-based assay for hcy quantitation is demonstrated.

TABLE 1

INTRA-ASSAY PRECISION

| hcy in serum (μm) | CV of 5 replicates signal (%) | CV of 5 replicates hcy concentration (%) |
|---|---|---|
| (1) with BABA in three-reagent protocol | | |
| 10 | 3.19 | 8.29 |
| 30 | 2.85 | 4.71 |
| 60 | 2.68 | 3.87 |
| (2) with CABA-phosphate on two-reagent protocol | | |
| 10 | 1.98 | 5.95 |
| 30 | 1.07 | 2.68 |
| 60 | 1.41 | 3.39 |

TABLE 2

STABILITY OF BABA (5 mM) STORED AT DIFFERENT pH BUFFER
(DETECTION OF HOMOCYSTEINE IN SERUM @ 2%)

(1) 4° C.

| pH | Fresh soln. % Signal Mod. | 3 wk soln. % Signal Mod. | 4 wk soln. % Signal Mod. | 7 wk soln. % Signal Mod. |
|---|---|---|---|---|
| 5 | 59 | 58 | 53 | 41 |
| 6 | 60 | 58 | 55 | 50 |
| 7 | 60 | 59 | 55 | 47 |

(2) R.T.

| pH | 3 wk soln. % Signal Mod. | 4 wk soln. % Signal Mod. | 7 wk soln. % Signal Mod. |
|---|---|---|---|
| 5 | 14 | 31 | 11 |
| 6 | 58 | 50 | 40 |
| 7 | 57 | 49 | 37 |

(3) 37° C.

| pH | 3 wk soln. % Signal Modulation |
|---|---|
| 5 | 7 |
| 6 | 41 |
| 7 | 38 |

TABLE 3

STABILITY OF CABA-PHOSPHATE STORED AT TWO TEMPERATURES
(5 mM in 50 mM BORATE BUFFER pH 9.0)

| Time Point | o/n | 1 wk | 2 wks | 5 wks | 7 wks | 10 wks | 13 wks |
|---|---|---|---|---|---|---|---|
| (1) Stored @4° C. | | | | | | | |
| Bo(x e5) | 5.577 | 5.682 | 5.587 | 5.569 | 5.999 | 6.047 | 5.87 |
| % Modula- | 57 | 54 | 56 | 55 | 54 | 51 | 45 |

TABLE 3-continued

STABILITY OF CABA-PHOSPHATE STORED AT
TWO TEMPERATURES
(5 mM in 50 mM BORATE BUFFER pH 9.0)

| Time Point | o/n | 1 wk | 2 wks | 5 wks | 7 wks | 10 wks | 13 wks |
|---|---|---|---|---|---|---|---|
| tion (0 to 60 µM) | | | | | | | |
| (2) Stored @37° C. | | | | | | | |
| Bo(x e5) | 5.980 | 5.287 | 5.945 | 6.102 | 6.073 | 6.699 | 6.98 |
| % Modulation (0 to 60 µM) | 55 | 45 | 51 | 50 | 51 | 44 | 35 |

TABLE 4

ASSAY CORRELATION STUDIES

| Methods | Numbering Samples (2%) | slope | r value |
|---|---|---|---|
| a. Three-reagent protocol | | | |
| LOCI vs. HPLC (BABA in 3Reagents's) | 50 | 1.009 | 0.933 |
| LOCI vs. HPLC (CABA-Phos. in 3Reagent's) | 50 | 1.050 | 0.910 |
| b. Two-reagent protocol | | | |
| LOCI vs. HPLC (CABA-Phos. in 2Reagent's) | 50 | 1.239 | 0.960 |

Example 3

EIA for the Determination of Homocysteine in Serum/Plasma

A. Materials

An enzyme immunoassay (EIA) for homocysteine (hcy) is typically performed according to standard procedures, essentially as follows. The following components may be used, for example: non-coated tubes; streptavidin coated microtiter plates; a reducing reagent (e.g., TCEP) in water; CABA-phosphate in buffer; alkaline phosphatase solution; a solution of anti-homocysteine-ABA monoclonal antibody conjugated with biotin; a solution of homocysteine-ABA conjugated to horseradish peroxidase (HRP), HRP substrate solution, and wash buffer. Homocysteine calibrators are preferably prepared by spiking known concentrations of the analyte to serum or plasma pool according to standard protocols.

B. Procedure

First, 5 µl serum, plasma sample, or calibrator control is mixed with 10 µl of 10 mM TCEP in water, in sample preparation tubes. The mixture is incubated for 10 min. at 37° C. Next, 50 µl of 8 mM CABA-phosphate (in 0.1 M sodium phosphate buffer, pH 7.5) and 50 µl of alkaline phosphatase solution (1 mg/ml, in borate buffer pH 9.2) are admixed; the mixture is incubated for 5 min. at 37° C. 350 µl borate buffer (pH 9.0) is then added to the reaction mixture, and 100 µl of this diluted reaction mixture is transferred to a microtiter well coated with streptavidin. Next, 25 µl of biotin labeled anti-ABA-homocysteine monoclonal antibody (containing 2 picomoles antibody) is added to each microtiter well and the mixtures are incubated at room temperature for 20 min. with shaking.

25 µl of HRP-ABA-homocysteine conjugate (containing 0.15 µg of the enzyme conjugate) is added to each reaction mixture, and the mixtures are further incubated for 10 min. at room temperature with shaking. Then, the reaction mixtures are aspirated and the microtiter wells are washed with phosphate buffer containing 0.05% Tween 20.

HRP substrate solution (e.g., K-Blue from ELISA Tech.) is added to the washed wells, and color development is read following 10 to 30 min. incubation at room temperature, using a commercial microtiter plate reader. Color development is directly related to the amount of enzyme conjugate bound to the microtiter well through interaction with the antibody. The amount of enzyme conjugate bound is inversely related to the amount of homocysteine in the sample. The determination of homocysteine in the sample is calculated from a standard curve produced by the determination of calibrators (see below).

HRP-ABA-homocysteine conjugate is prepared by a procedure similar to that described for immobilization of ABA-homocysteine on solid surfaces. Biotin-labeled monoclonal antibody is prepared by methods known to those of skill in the relevant art.

Biotinylated Antibodies:

Anti-homocysteine-ABA monoclonal antibody (e.g., 15C12, from Dade Behring, Deerfield, Ill.) or any other suitable anti-hcy-ABA antibody is biotinylated essentially as follows. A total of 7.5 mg (9.75 mL) aliquot is dialyzed against 2×2 µL of 0.1 M NaHCO$_3$ (pH 8.0) in cold conditions, and concentrated on Centriprep 30 to a volume of 4.65 mL. The concentration is determined by UV (1.1 mg/mL) giving a recovery of 5.13 mg. Gel electrophoresis (e.g., Paragon gel electrophoresis) is used to confirm the presence of a single band.

Next, biotinamidocaporate N-hydroxysuccinimide ester is dissolved in DMSO at 13 mM and is then added to antibody solution to obtain 5:1, 10:1, and 25:1 molar ratios. 1.5 mg of the Ab is used for each preparation. After 2 hrs at room temperature in the dark, the reaction mixtures are dialyzed against 2×2 µL phosphate buffered saline (PBS; 10 mM Na$_2$HPO$_4$, 150 mM NaCl, pH 7.4) in cold conditions. Concentration is determined by UV. Products are stored refrigerated with 0.05% sodium azide.

Serum Calibrators:

Serum calibration curves are generated with known amounts of homocysteine spiked into serum samples generated by pooling sera from normal individuals (e.g., from 38 normal individuals). Serum calibrators are prepared with either depleted or untreated pooled serum. Homocysteine concentration is validated before and after the treatment by HPLC, e.g., at a reference lab.

The foregoing specification, including the specific embodiments and examples, is intended to be illustrative of the present invention and is not to be taken as limiting. Numerous other variations and modifications can be effected without departing from the true spirit and scope of the present invention.

What is claimed is:

1. A kit for use in a method for detecting and determining the amount of homocysteine in a sample, comprising in a packaged combination: a first reagent comprising an alkylating reagent having a haloketone or alpha haloaldehyde functional group, the carbonyl of said haloketone or alpha haloaldehyde functional group derivatized with a protected functional group said protected functional group capable of reacting with the sulfhydryl group of homocysteine to form modified homocysteine when said protected functional group is deprotected, a second reagent comprising an activating reagent capable of deprotecting said alkylating reagent by removal of the protected functional group, and a third reagent capable of specifically binding to said modified homocysteine, each in an amount sufficient to conduct at least one assay.

2. The kit of claim 1, wherein said first reagent further comprises a homocysteine disulfide reducing agent.

3. The kit of claim 1, wherein said first reagent further comprises a solid matrix coated with modified homocysteine.

4. The kit of claim 3, wherein said solid matrix comprises latex or glass beads.

5. The kit of claim 1 wherein said protected haloketone is CABA.

6. The kit of claim 1, wherein said second reagent is a phosphatase.

7. The kit of claim 6 wherein said phosphatase is alkaline phosphatase.

8. The kit of claim 1, wherein said second reagent further comprises a solid matrix coated with a receptor capable of specifically binding modified homocysteine.

9. The kit of claim 8, wherein said receptor is an antibody or an immunologically active fragment thereof.

10. The kit of claim 3 or 8, wherein said matrix further includes a signaling agent affixed thereto.

11. The kit of claim 10, wherein said signaling agent comprises a chemiluminescent agent, a fluorescent agent, or a chromogenic agent.

12. A method of determining the amount of homocysteine in a sample suspected of containing said homocysteine, comprising the steps of:
  (a) bringing together in an aqueous medium:
    (1) said sample,
    (2) a first reagent comprising an alkylating reagent having a haloketone or alpha haloaldehyde functional group, the carbonyl of said haloketone or alpha haloaldehyde functional group derivatized with a protected functional group capable of being activated to chemically modify the sulfhydryl groups of homocysteine to form modified homocysteine, and
    (3) a second reagent comprising an antibody capable of specifically binding to said modified homocysteine to from an immunocomplex; and
    (4) a third reagent capable of activating said protected alkylating reagent.
  (b) measuring the amount of said immunocomplex, the amount thereof being related to the amount of homocysteine in said sample.

13. The method of claim 12, wherein said first reagent further comprises a disulfide reducing agent.

14. The method of claim 12, wherein said third reagent is a phosphatase.

15. The method of claim 14, wherein said phosphatase is alkaline phosphatase.

16. The method of claim 12, wherein said first reagent further comprises a solid matrix coated with hcy-ABA.

17. The method of claim 12, wherein said first reagent further comprises a solid matrix coated with a receptor capable of binding modified homocysteine.

18. The method of claim 16 or 17, wherein said solid matrix comprises latex or glass beads.

19. The method of claim 16 or 17, wherein said solid matrix comprises a microtiter plate.

20. A method of determining the amount of homocysteine in a sample, wherein at least a portion of said homocysteine is in the free disulfide form, comprising the steps of:
  (a) preparing an admixture comprising:
    (1) said sample,
    (2) a releasing agent to release said homocysteine from the disulfide form,
    (3) an alkylating reagent having a haloketone or alpha haloaldehyde functional group, the carbonyl of said haloketone or alpha haloaldehyde function group derivatized with a protected functional group capable of being activated to chemically modify the sulfhydryl groups of homocysteine to form modified homocysteine, and
    (4) an antibody capable of specifically binding to said modified homocysteine to form an immunocomplex, and
    (5) an activating reagent capable of deprotecting said protected functional group of said alkylating reagent; and
  (b) examining said medium for the amount of said immunocomplex, the amount thereof being related to the amount of homocysteine in said sample.

* * * * *